(12) United States Patent
Khouri et al.

(10) Patent No.: US 11,540,894 B2
(45) Date of Patent: Jan. 3, 2023

(54) RIGIDITYING BRACE

(71) Applicant: Lipocosm, LLC, Key Biscayne, FL (US)

(72) Inventors: Roger K. Khouri, Key Biscayne, FL (US); Khalil R. Khouri, Key Biscayne, FL (US); Thomas Morgan Biggs, Jr., Houston, TX (US)

(73) Assignee: LIPOCOSM, LLC, Key Biscayne, FL (US)

( * ) Notice: Subject to any disclaimer, the term of this patent is extended or adjusted under 35 U.S.C. 154(b) by 0 days.

(21) Appl. No.: 17/719,446

(22) Filed: Apr. 13, 2022

(65) Prior Publication Data

US 2022/0233269 A1   Jul. 28, 2022

Related U.S. Application Data

(63) Continuation-in-part of application No. 17/268,302, filed as application No. PCT/US2019/054890 on Oct. 4, 2019.

(Continued)

(51) Int. Cl.
*A61B 90/00* (2016.01)
*A41C 3/00* (2006.01)
(Continued)

(52) U.S. Cl.
CPC ............ *A61B 90/02* (2016.02); *A41C 3/0064* (2013.01); *A61F 2/52* (2013.01); *A61F 5/03* (2013.01);
(Continued)

(58) Field of Classification Search
CPC ...... A61F 5/03; A61F 13/145; A61F 5/05833; A61F 13/20; A41C 3/0064; A61B 5/6862;
(Continued)

(56) References Cited

U.S. PATENT DOCUMENTS

| 936,434 A | 10/1909 | Eganhouse |
|---|---|---|
| 3,382,867 A | 5/1968 | Reaves |

(Continued)

FOREIGN PATENT DOCUMENTS

| CA | 2 827 067 | 8/2012 |
|---|---|---|
| CH | 396 311 | 7/1965 |

(Continued)

OTHER PUBLICATIONS

PCT/US2019/0654890 International Search Report (dated Dec. 23, 2019).

(Continued)

*Primary Examiner* — Tarla R Patel
(74) *Attorney, Agent, or Firm* — Neil D. Gershon

(57) ABSTRACT

A brace for retaining an organ in an expanded state configured to adhere and substantially conform to an external surface of the organ includes an inner layer, an outer layer, and at least one sheet of thin malleable material forming a middle layer between the inner layer and outer layer, the at least one sheet being enclosed and configured to rigidify and maintain the organ in an expanded state upon application of a vacuum. The brace can be incorporated into a brassiere.

19 Claims, 16 Drawing Sheets

Related U.S. Application Data

(60) Provisional application No. 63/175,611, filed on Apr. 16, 2021, provisional application No. 62/741,516, filed on Oct. 4, 2018.

(51) Int. Cl.
*A61F 13/14* (2006.01)
*A61F 2/52* (2006.01)
*A61F 5/03* (2006.01)
*A61F 5/058* (2006.01)
*A61H 9/00* (2006.01)

(52) U.S. Cl.
CPC ........ *A61F 5/05833* (2013.01); *A61F 13/145* (2013.01); *A61H 9/0057* (2013.01); *A61H 2201/1238* (2013.01); *A61H 2201/165* (2013.01); *A61H 2201/169* (2013.01); *A61H 2201/1619* (2013.01); *A61H 2201/1645* (2013.01); *A61H 2201/5071* (2013.01); *A61H 2205/082* (2013.01)

(58) Field of Classification Search
CPC .... A61B 17/12118; A61B 2017/32096; A61B 17/12159
See application file for complete search history.

(56) References Cited

U.S. PATENT DOCUMENTS

| | | | |
|---|---|---|---|
| 4,848,364 A * | 7/1989 | Bosman | A61B 90/00 128/850 |
| 5,415,620 A | 5/1995 | Chen | |
| 5,536,233 A | 7/1996 | Khouri | |
| 5,662,583 A | 9/1997 | Khouri | |
| 5,676,634 A | 10/1997 | Khouri | |
| 5,695,445 A | 12/1997 | Khouri | |
| 5,701,917 A | 12/1997 | Khouri | |
| 6,042,537 A | 3/2000 | Kaiser | |
| 6,074,399 A | 6/2000 | Wallace et al. | |
| 6,478,656 B1 | 11/2002 | Khouri | |
| 6,500,112 B1 | 12/2002 | Khouri | |
| 6,641,527 B2 * | 11/2003 | Khouri | A61B 90/02 600/38 |
| 6,699,176 B1 | 3/2004 | Khouri | |
| 6,949,067 B1 | 9/2005 | Dann et al. | |
| 7,909,805 B2 | 4/2011 | Wang et al. | |
| 8,485,192 B2 | 7/2013 | Davidson et al. | |
| 9,066,795 B2 | 6/2015 | Khouri et al. | |
| 9,498,565 B2 | 11/2016 | Nowroozi et al. | |
| 9,522,058 B2 | 12/2016 | Khouri et al. | |
| 10,433,947 B2 | 10/2019 | Khouri et al. | |
| 10,603,161 B2 | 3/2020 | Horne et al. | |
| 2001/0031911 A1 | 10/2001 | Khouri | |
| 2003/0073951 A1 | 4/2003 | Morton et al. | |
| 2005/0008669 A1 | 1/2005 | Chen | |
| 2005/0059853 A9 | 3/2005 | Kochamba | |
| 2005/0245850 A1 | 11/2005 | Freyre et al. | |
| 2005/0267386 A1 | 12/2005 | Copelan | |
| 2006/0106334 A1 | 5/2006 | Jordan et al. | |
| 2007/0055179 A1 | 3/2007 | Deem | |
| 2007/0149991 A1 | 6/2007 | Mulholland | |
| 2009/0042477 A1 | 2/2009 | Redenius | |
| 2009/0177134 A1 | 7/2009 | Timothy | |
| 2011/0251602 A1 | 10/2011 | Anderson | |
| 2011/0313412 A1 | 12/2011 | Kim et al. | |
| 2012/0310126 A1 * | 12/2012 | Bureau | A61F 5/05833 602/6 |
| 2014/0094722 A1 | 4/2014 | Wu | |
| 2014/0288646 A1 | 9/2014 | Khouri et al. | |
| 2014/0378946 A1 | 12/2014 | Thompson | |
| 2015/0328380 A1 | 11/2015 | Furrer et al. | |
| 2016/0000551 A1 | 1/2016 | Khouri et al. | |
| 2016/0324666 A1 | 11/2016 | Barberio | |
| 2017/0196756 A1 | 7/2017 | Palomaki | |
| 2017/0296422 A1 | 10/2017 | Park et al. | |
| 2017/0341334 A1 * | 11/2017 | Corrigan | B32B 15/095 |
| 2018/0021492 A1 | 1/2018 | Furrer et al. | |
| 2020/0375839 A1 | 12/2020 | Kim et al. | |
| 2020/0405925 A1 | 12/2020 | Koster et al. | |
| 2021/0046227 A1 | 2/2021 | Bakker-Van Der Kamp et al. | |
| 2021/0060220 A1 | 3/2021 | Chang et al. | |
| 2021/0220535 A1 | 7/2021 | Ochiai et al. | |

FOREIGN PATENT DOCUMENTS

| | | |
|---|---|---|
| CN | 103689822 | 4/2014 |
| CN | 108042862 | 5/2018 |
| EP | 2 377 475 | 10/2011 |
| JP | H 1052886 | 2/1998 |
| WO | WO 01/58361 | 8/2001 |
| WO | WO 2005/079612 | 9/2005 |
| WO | WO 2017/165215 | 9/2017 |
| WO | WO 2017/220997 | 12/2017 |
| WO | WO 2020/073021 | 4/2020 |

OTHER PUBLICATIONS

PCT/US2021/060680 International Search Report (dated Feb. 18, 2022).
Supplementary European Search Report Application No. EP 13 78 5140 dated Feb. 18, 2021.
Supplementary European Search Report Application No. EP 19 86 8805 dated Nov. 19, 2021.
www.amazon.com/Motherlove-Certified-Organic-Cracked-Nursing/dp/B0007CQ726.

* cited by examiner

RIGIDITYING BRACE

CROSS-REFERENCE TO RELATED APPLICATIONS

This application claims priority to provisional application Ser. No. 63/175,611, filed Apr. 16, 2021 and is a continuation in part of application Ser. No. 17/268,302, filed Feb. 12, 2021, which is a 371 of PCT application PCT/US2019/054890, filed Oct. 4, 2019, which claims the benefit of priority of U.S. Provisional Patent Application No. 62/741,516, filed Oct. 4, 2018. The entire contents of each of these applications are incorporated herein by reference.

TECHNICAL FIELD

The present disclosure relates to a rigidifying adherent conforming brace and corresponding methods for retaining an organ in an expanded state.

BACKGROUND

Generally, edema and tissue swelling are considered pathologic conditions to be treated by medical interventions, such as compression garments. However, in some instances, inducing and maintaining a chronic edema state may be beneficial when the desired goal is to ultimately induce tissue augmentation and enlargement through induction of fat formation as a result of that chronic edema state. For example, the applicant has previously developed devices and techniques for manipulating and molding soft tissue with active external tissue expanders like the Brava Bra for breast expansion/augmentation (see, for example, U.S. Pat. Nos. 5,536,233; 5,662,583; 5,676,634; 5,695,445; 5,701,917; 6,478,656; 6,500,112; 6,641,527; and 6,699,176, all of which are incorporated herein by reference in their entirety) or the external passive expander splint (see, for example, U.S. Pat. Nos. 9,066,795 and 9,522,058, both of which are incorporated herein by reference in their entirety).

Existing compression bandages apply external compressive forces to soft tissue, which counteract any distention induced by such devices and techniques. For example, laces, straps, or other components may immobilize the soft tissue. Existing passive splints also often conform to the treated body part and have a rigidifying layer that stiffens the construct to preserve and maintain the soft tissue until healing ensues. The rigidifying factors in these existing devices often rely on curing or polymerization of a chemical. Some of these prior art devices do rely on vacuum to rigidify, but do not include an adhesive component that can counteract the recoil forces of an iatrogenic swollen state. Furthermore, while some prior art devices are malleable to conform with the splinted extremity, they lack the ability to not only conform but also expand its surface area in two dimensions in order to embrace different levels of tissue swelling.

Achieving rigidity by polymerization of a chemical is a one-time, irreversible process. Additionally, braces that achieve rigidity induced by physical agents, such as temperature, face mechanical phase variations.

Therefore, it would be advantageous to provide a device and method for bracing and retaining distended tissue that can rigidify, soften to become malleable, and rigidify again multiple times, and at each step, obtain as needed varying degrees of rigidity over different surface areas and tissue contours while adhering to the swollen tissue to prevent its deflation. For certain applications, it would also be advantageous to reduce its bulk to maximize the concealability of the brace.

Commonly owned PCT application PCT/2019/054890 (WO 2020/073021), filed Oct. 4, 2019, discloses devices and techniques for bracing distended tissue and retaining organs in expanded states. The devices and methods advantageously achieve this without requiring polymerization. The devices and methods disclosed use various materials sandwiched between two layers which are hardened by vacuum. Although effective, there is room for improvement to the devices including improving its securement to the patient's skin, its concealability and its malleability as well as minimizing adverse affects on the skin during the vacuum application.

SUMMARY

The present invention provides innovative enhancement/improvements to the devices and techniques for bracing distended tissues and retaining organs in expanded states such as disclosed in commonly owned PCT application WO 2020/073021, the entire contents of which are incorporated herein by reference. Inventors of the present invention, who are also inventors of the PCT application WO2020/073021, discovered that although effective, the devices of the PCT application had some drawbacks to address to improve the function and certain clinical applications of the device. As described below, the inventors of the present application conceived innovative ways to improve the securement of the device to the patient, to improve the concealability of the device, which has particular advantages when used for example as a brassiere, and to improve its malleability. Furthermore, the inventors of the present invention conceived of innovative ways to minimize irritation and wrinkling of the skin, which is particularly important in cosmetic surgery.

The devices and methods disclosed herein preserve iatrogenically or otherwise induced swollen tissue conditions while remaining passive. In addition, the devices and methods disclosed herein prevent the natural tendency of distended and expanded tissues and organs to recoil, which may allow for maintaining a potentially beneficial chronic swelling or edema.

The devices and methods disclosed herein use select materials to rigidify the device, thereby avoiding certain drawbacks of existing compression bandages. The materials can rigidify via interlocking of rough surfaces. Alternatively, or in addition, the multiple layers of the material can be compressed together to form a rigid laminate structure. The interlocking and/or compression is achieved via application of vacuum as discussed below. Achieving rigidity by polymerization of a chemical under current methods is a one-time, irreversible process, whereas the devices and methods of the inventions disclosed herein can be used multiple times and at varying degrees of rigidity. Additionally, braces that achieve rigidity induced by physical agents, such as temperature, face mechanical phase variations. In contrast to these prior art processes, embodiments of the present disclosure rely upon fluid aspiration to interlock (and/or compress) the loosely textured components of the rigidifying layer to stiffen it, as depicted in FIG. 1.

In preferred embodiments of the present invention, materials are sandwiched between two or more layers, and the materials are transformed from soft and malleable to hard and rigid via application of negative pressure. In preferred embodiments, the materials utilized provide the widest spectrum from soft and fully malleable to work hard rigid, and at the lowest vacuum pressure and the least material thickness. Such materials are discussed in detail below. These materials strike the optimal balance of several factors: softest prior to rigidifying, very conforming to the body prior to application of vacuum (before rigidification), hard material when transitioned, thinness for concealability and sufficiently malleable and expansile in surface area. Furthermore, since the surface area of the inner layer in contact with the skin necessarily varies with the degree of swelling and tissue distension, the potentially resultant folds of the reduced surface area are preferably buffered or dampened so as not to induce wrinkles and pressure ridges on the underlying skin.

The buffer layer in contact with the skin may be a soft stretchable fabric or sponge like material thick enough to dampen the effects of the inner layer folds pressed against the skin. The buffer layer can also be a gel, a very low durometer rubber, or a fluid that would best transmit an evenly contoured pressure points free adhesion between skin and inner layer regardless of the contour convolutions of the inner layer. The interposed gel layer in itself may have adhesive properties that connect the skin to the inner layer and provide the required isotropic counter-deflation effect.

In the following description, certain aspects and embodiments will become evident. It should be understood that the aspects and embodiments, in their broadest sense, could be practiced without having one or more features of these aspects and embodiments. It should be understood that these aspects and embodiments are merely exemplary.

In accordance with one aspect of the disclosure, a device is provided in the form of a passive stent, also referred to herein as a brace or passive brace, for retaining an organ in an expanded state. The passive stent comprises an inner layer, an outer layer and a middle layer enclosed by the inner layer and the outer layer which includes a plurality of components configured to interlock and become a thinner compressed laminate upon application of a vacuum.

In some embodiments, the middle layer may be configured to substantially conform to an external surface contour of the organ before interlocking. Additionally, the middle layer may be configured to maintain the shape and volume of an organ in its expanded state after interlocking.

In some embodiments, the middle layer may comprise at least one of foam or putty. The at least one of foam or putty may be textured and may comprise textured polyurethane and/or textured polybutene. Additionally or alternatively, the middle layer may comprise a plurality of strips comprising sponge or cellulose. Additionally or alternatively, the middle layer may comprise at least one fibrous material that can stretch and interlock upon compression. For example, the at least one fibrous material may comprise paper, such as sandpaper. In alternate embodiments, the middle layer may comprise one or more sheets of very thin and smooth paper and stretchy paper-like material.

Additionally, or alternatively, the middle layer may comprise a plurality of sheets or strips of malleable and/or stretchable fabric.

Additionally or alternatively, the middle layer may comprise a gel with fibers. In such embodiments, the fibers may comprise at least one polyester, polystyrene, or other plastic. Additionally or alternatively, the middle layer may comprise a gel with beads. In such embodiments, the beads may comprise microbeads. In some embodiments, the rigidification may require negative pressure aspiration of the fluid in the middle layer.

In accordance with another aspect of the present disclosure, a brace for retaining an organ of a patient in an expanded state is provided comprising an inner layer, an outer layer and at least one sheet of paper forming a middle layer between the inner layer and outer layer, the at least one sheet of paper being enclosed and configured to rigidify upon application of a vacuum.

The at least one sheet of paper is preferably very soft and malleable prior to application of vacuum.

In some embodiments, each sheet of paper has a thickness of about 1/1000 inch, although other thicknesses are also contemplated. The at least one sheet of paper is moldable to a contour of a patient's body. In some embodiments, the sheet(s) is/are smooth and devoid of irregularities on its surface. In some embodiments, the sheet(s) of paper is/are corrugated, wrinkled, and/or accordion folded prior to being stacked. In some embodiments, the at least one sheet of paper comprises a plurality of sheets of paper having a combined thickness of between about 15 mm to about 40 mm prior to rigidifying by vacuum and once rigidified, have a combined thickness significantly less.

The inner layer is configured in preferred embodiments to adhere to the surface of the organ being braced by using one or more of surface tension, vacuum or adhesive.

A port can be provided which is configured for applying the vacuum or aspirating the fluid in the middle layer through at least one of the inner layer and the outer layer. In some embodiments, tubing having a plurality of perforations and extending into the middle layer communicates with the port. The multiple perforations reduce the chance of blockage of vacuum since if one perforation is clogged, vacuum can still be applied through other perforations. An alternative/adjunct to multiple perforations to reduce the chance of leaflet valve effect vacuum blockage is the inclusion of a string inside the tube and at the tip of the port.

In some embodiments, the inner layer is configured to contact the organ; in other embodiments, an additional padding layer is attached to the inner layer, the padding providing a buffering layer configured to contact and adhere to the organ and limit imprint from the inner layer wrinkles on the surface, e.g., organ or skin, of the patient. That padding could be for example a stretchable textured fabric, a stretchable sponge, a gel, or a liquid layer.

In some embodiments, the outer layer has a rim about at least a portion of its periphery and the device further comprises an adhesive sheet placed over and attached to a least a portion of the rim and extending outwardly from the rim for attaching and providing an air tight seal. Such sheet maintains the adhesive attachment outside the region where vacuum is applied to the organ.

According to another aspect of the present disclosure, a device for retaining an organ of a patient in an expanded state is provided comprising an inner layer, an outer layer having a rim about at least a portion of a periphery and at least one or more components forming a middle layer between the inner layer and outer layer, the at least one or more components being enclosed and configured to rigidify upon application of a vacuum. A cover is attached to a least a portion of the rim of the outer layer, the cover having an adhesive and extending radially outwardly from the rim to adhesively attach to the skin such that the organ expanded by vacuum is devoid of adhesive.

In some embodiments, the cover is in the form of donut-shaped sheet having an opening to expose the outer layer. In some embodiments, the inner surface of the cover is covered by peel away layer of material. In some embodiments, the cover is removable and replaceable by another cover.

In accordance with another aspect of the present disclosure, a device for retaining an organ of a patient in an expanded state is provided comprising an inner layer, an outer layer, and at least one or more components forming a middle layer between the inner layer and outer layer. The at least one or more components is enclosed and configured to rigidify upon application of negative pressure, e.g., a vacuum, and the application of negative pressure forcefully reduces the radial thickness of the one or more components of the middle layer. A tubing is positioned within the middle layer, the tubing having a plurality of openings for applying vacuum to the middle layer to rigidify the one or more components.

Negative pressure (whether vacuum or forceful aspiration of the contained fluid) forcefully presses the components of the middle layer together. Friction then prevents the various components from sliding past each other and the lamination effect causes the layer to become stiff.

In some embodiments, the tubing has a curved, i.e., non-linear, configuration.

In some embodiments, the tubing includes a semi-rigid string to prevent leaflet valve effect obstruction from the vacuum.

In some embodiments, the device is flexible and stretchable such that its surface area can expand in two dimensions, and the middle layer is configured to substantially conform to the variable contour and size of the organ external surface before interlocking and/or compression. In some embodiments, the middle layer is configured to maintain the organ in the expanded state after interlocking/compression.

In some embodiments, the device is connected to a gel filled donut ring that interfaces with the patient's tissues to distribute any counterforce effect, reduce pressure points, and if adhesive, help maintain an airtight seal. Still in some other embodiments, the device is connected to a concave deflective rubber rim that can espouse the contour of the surrounding tissues to maintain the vacuum. Furthermore, a vacuum pump with a servo-controlled mechanism might be necessary to restore the vacuum in the event of occasional air leaks.

According to another aspect of the disclosure, a device in the form of a passive stent (brace) is provided for retaining an organ in an expanded state. The device includes a plurality of components configured to interlock and/or compress upon application of a vacuum. The device is in the form of a rigidifying dome mounted on a rim designed to interface with the patient skin at the periphery of the area to be maintained swollen. An adhesive film may be attached to the outer layer. In preferred embodiments, the adhesive film extends beyond the periphery of the inner layer to help maintain it in place and to preserve the vacuum seal.

In some embodiments, the adhesive film forms a donut sheet that sticks to a rim of the stent.

In some embodiments, the stent has an inner layer, an outer layer and a middle layer enclosed by the inner layer and the outer layer, and the components are in the middle layer.

In any of the embodiments described above, the inner layer may be configured to adhere to the organ using surface tension. Additionally or alternatively, the inner layer may be configured to adhere to the organ upon application of a vacuum to a volume (e.g., a volume of air) between the inner layer and a surface of the organ. Accordingly, the brace may further comprise a port allowing for application of the vacuum to the volume through at least the inner layer. The port might include a one-way valve to prevent air re-entry and maintain the vacuum. The port may be connected to a portable battery-operated pump with a servo-control mechanism to preserve the vacuum and restore it as necessary. Additionally, or alternatively, the inner layer may be configured to adhere to the organ using at least one adhesive layer between the inner layer and a surface of the organ. Alternatively, the contact between the inner layer and the skin might be preserved by surface tension forces.

In any of the embodiments described above, the brace may further comprise a port allowing for application of the vacuum to the middle layer through at least one of the inner layer and the outer layer. In some embodiments, one or more tubes with multiple openings is connected to (in communication with) the port and extends into the middle layer to reduce the chances of occlusion and thus maintain the vacuum for rigidifying the material of the middle layer. A pump might be utilized to preserve and restore that negative rigidifying pressure in the event of pressure loss.

The device can have various clinical applications. In one such application, the device is used for breast expansion/augmentation and can be applied to a breast of the patient. The device can also be in the form of a brassiere. In such embodiments, the brassiere can comprise one cup in the form of the rigidifying device for a single breast, e.g., for use in mastectomy patients, or can comprise two cups, each cup configured to support a breast. Each cup may comprise an inner layer, an outer layer and a middle layer enclosed by the inner layer and the outer layer and having one or more components configured to rigidify (via interlocking and/or compression) upon application of a vacuum. A port is provided to allow the application of the vacuum to the middle layer. The middle layer is preferably configured to substantially conform to an external surface of the breast before rigidifying and to maintain the breast in the expanded state after rigidifying.

In such embodiments, the brassiere may further have a semi-rigid frame defining peripheries of the one cup or two cups and configured to secure the one cup or two cups to peripheries of the breasts. The frame might be a gel filled donut structure or a semi-rigid rubber skirt designed to conform to the body surface topography, dissipate any counter-force, diffuse the counter-pressure on the surrounding tissue, and help maintain an air-tight seal. Additionally or alternatively, the brassiere may further have a peripheral extension surrounding at least a portion of the cup(s) and configured to block airflow between the inner layer and skin of the breasts. In some embodiments, the extension is shirt-like. Additionally or alternatively, the brassiere may further comprise fabric configured to conform to a torso and block airflow between the inner layer and skin of the breasts. In some embodiments, the fabric conforms to the torso and the breasts. In some embodiments, a donut-like sheet is adhesively attached to the rim of each cup and to the skin outside the periphery of the rim.

In accordance with another aspect of the present disclosure, a brassiere is provided comprising at least one cup, i.e., one or two cups, each cup configured to support a breast and each cup including an inner layer, an outer layer and a middle layer formed by at least one soft sheet of paper configured to rigidify upon application of a vacuum. The middle layer is configured to substantially conform to the external surface and volume of the breasts before rigidifying and is configured to maintain the breasts in the expanded state and prevent them from losing shape or volume after rigidifying.

In accordance with another aspect of the present disclosure, a brassiere is provided comprising at least one cup, i.e., one or two cups, each cup configured to support a breast and each cup including an inner layer having a region defining a closed area for application of vacuum to induce a distractive force to place the breast in an expanded state, an outer layer and a middle layer formed by at least one or more components configured to rigidify upon application of a vacuum. The middle layer is configured to substantially conform to an external surface of the breasts before rigidifying and is configured to maintain the breasts in the expanded state after rigidifying. The brassiere can be adhesively attached to a skin of the breast wherein the adhesive is outside the closed area in which vacuum is applied.

In some embodiments, the outer layer has a rim around a periphery thereof, and the brassiere is attached to the skin via a cover placed over the rim, the sheet having an adhesive on an inner surface. The cover, in some embodiments, has an opening to form a donut shape, the opening exposing the cup of the brassiere.

As noted above, the device disclosed herein can have one cup (e.g., dome) for a single breast or have two cups (e.g., two domes) for augmentation of both breasts of a patient. The device can also have application for augmentation of other body parts and organs such as for penile augmentation by way of example.

In accordance with another aspect of the present disclosure, a method for retaining an organ in an expanded state is provided. In such embodiments, the method comprises applying at least some internal or external force, or other effect/process to the organ to place the organ in the expanded state, applying a passive stent to an external surface of that enlarged organ, wherein the passive stent comprises at least one layer comprising a plurality of components, and applying a vacuum to the passive stent sufficient to rigidify (e.g., via interlocking and/or compression) the plurality of components in the at least one layer. The at least one layer may be configured to maintain the organ in the expanded state after interlocking. In some embodiments, the organ may comprise a breast.

In accordance with another aspect, the present disclosure provides a method for retaining an organ of a patient in an expanded state comprising:

providing a brace having an inner layer, an outer layer and a middle layer positioned between the inner layer and outer layer, the middle layer comprising at least one or more soft components;

applying a cover to the brace, the cover extending beyond a periphery of the device;

applying a vacuum to provide a fluid tight seal of the cover to the skin; and subsequently applying negative pressure to the middle layer to rigidify the one or more soft components.

In any embodiments described above, applying the passive stent may comprise adjusting a morphology of the passive stent to substantially conform to a morphology of the external surface.

In any embodiments described above, applying the vacuum may comprise applying suction to a port of the passive stent such that fluid, e.g., gas, is removed from the at least one layer of the passive stent.

Exemplary objects and advantages will be set forth in part in the description that follows, or may be learned by practice of the exemplary embodiments. It is to be understood that both the foregoing general description and the following detailed description are exemplary and explanatory only and are not restrictive of the invention, as claimed.

BRIEF DESCRIPTION OF DRAWINGS

So that those having ordinary skill in the art to which the subject invention appertains will more readily understand how to make and use the surgical apparatus disclosed herein, preferred embodiments thereof will be described in detail hereinbelow with reference to the drawings, wherein.

DETAILED DESCRIPTION

Figure 1:
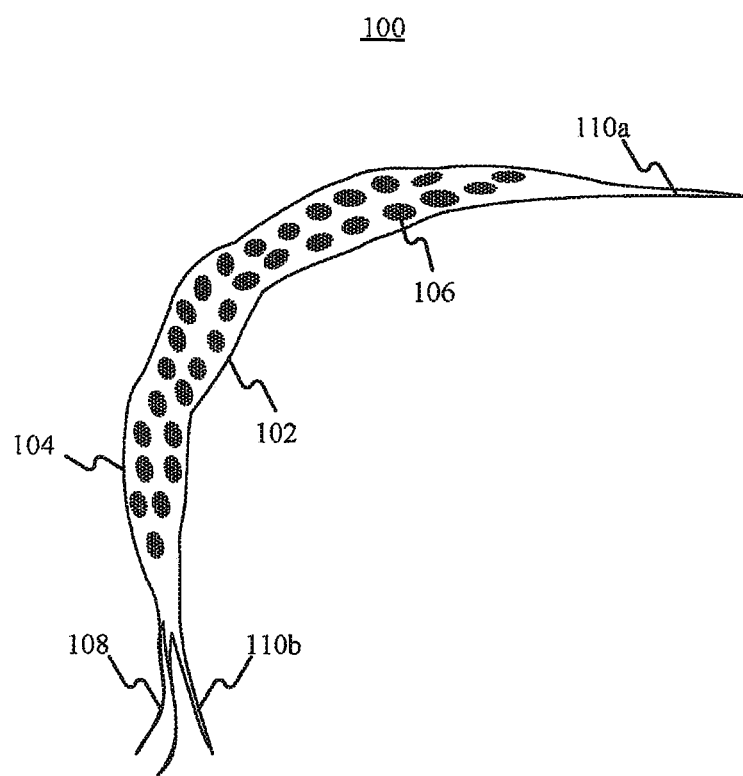
FIG. 1 is a schematic representation of a rigidifying brace according to an embodiment of the present disclosure.

The devices and methods disclosed herein preserve iatrogenically or otherwise induced swollen tissue conditions while remaining passive. In addition, the devices and methods disclosed herein in certain applications prevent the natural tendency of distended and expanded tissues and organs to recoil, which allow for maintaining a potentially beneficial chronic swelling or edema. This is achieved via a rigidifying layer of material as described below. This rigidifying layer is positioned between an outer layer and an inner layer, and is preferably enclosed for effective application of vacuum or negative pressure thereto.

The present invention provides innovative enhancements/improvements to the devices and techniques for bracing distended tissues and retaining organs in expanded states such as disclosed in commonly owned PCT application WO 2020/073021 (hereinafter the "073021 application"). There are several enhancements to the devices of this PCT application which include one or more of: 1) use of a smooth, thin and malleable sheets of paper-like material as the middle layer for conformance to the surface of the organ; 2) use of a cover to reduce adhesive to the area of skin under vacuum; 3) use of a padding layer to provide a buffer to reduce the effect of wrinkling of the inner layer and impart to the skin an even contact surface to avoid high pressure contact points or ridges and to improve cosmetics; and/or 4) use of tubing to reduce the chance of occlusion of the vacuum inlet to the middle layer. It should be appreciated that the devices of the present invention need not have all four of these features since each feature alone is advantageous. Thus, it is contemplated that the devices can have one, two, three or all four of these listed features. Each of these features is discussed in more detail below.

As noted above, the inventor of the present invention, who is also the inventor of the 073021 PCT application, discovered that although effective, the devices of the 073021 PCT application had some drawbacks which would be beneficial to address to improve the function and clinical applications of the device. As described below, utilizing one or more of the four aforementioned listed features, the inventors of the present application improved the securement of the device to the patient, improved the malleability of the device and improved the concealability of the device, which has particular advantages when used for example as a brassiere. Furthermore, the inventors of the present invention conceived of innovative ways to minimize irritation and wrinkling of the skin in contact with the inner layer, which is particularly important in cosmetic surgery.

The "device" of the present disclosure is also referred to herein as a "passive stent" or a "stent" or a "brace" or a "passive brace' as it functions to prevent deflating of tissue that is iatrogenically swollen. Thus, these terms are used interchangeably herein.

The devices of the present invention can be used for various clinical applications. One example is for use as a brassier for breast enlargement/augmentation or for breast reconstruction and correction of congenital deformities. This use is described in detail below by way of example, and illustrated in several of the drawings. Another use by way of example is for penile enlargement.

Note the term fluid used herein includes a liquid and/or gas.

The devices and methods disclosed herein use materials which interlock and/or compress to rigidify the device. While some existing bandages and splints also use vacuum to rigidify, they are designed to compress and immobilize the part being treated. This invention is designed to have the opposite effect. In contradistinction to these prior devices designed to apply a compressive immobilizing force, this device applies a counterforce that acts against the deflation force of the swollen organ and therefore places the tissues under tension. Its inner surface has adhesive properties that counteract the forces of recoil and forces the enlarged organ to maintain its expanded state. Furthermore, while some of the existing bandages and splints that rigidify with the application of vacuum are also foldable and malleable, these devices do not have design features that allow them to stretch and enlarge their surface area in two dimensions in order to treat organs in various levels of expansion from a flat disk-like surface to a highly swollen deeply expanded dome.

As noted above, achieving rigidity by polymerization of a chemical as in the prior art is a one-time, irreversible process. In contrast, the devices and methods disclosed herein may be used multiple times, if desired, and at varying degrees of rigidity. The varying degrees of rigidity can be achieved by vacuum levels or alternatively achieved by the material utilized for the middle layer. Additionally, braces that achieve rigidity induced by physical agents, such as temperature, face mechanical phase variations. In contrast to these prior art processes, embodiments of the present disclosure rely upon fluid aspiration to compress together the soft components of the middle layer to form a stiff laminate structure and/or to interlock the loosely textured components of the rigidifying middle layer to stiffen it, as depicted in FIG. 1.

In the present disclosure, materials are sandwiched between two or more layers, and the materials are transformed from soft and malleable to hard and rigid via vacuum. In preferred embodiments, the materials utilized provide the widest spectrum from soft and fully malleable to word hard rigid at the lowest vacuum pressure and the least material thickness. Such materials are discussed in detail below. These materials strike the optimal balance of several factors: transition from soft to hard material, thinness for concealability and sufficiently malleable, expandable, and stretchable prior to stiffening.

The devices of the present disclosure are in the form of a passive stent for retaining an organ in an expanded state. The device has an inner layer and an outer layer, inner denoting closer to the wearer's skin and outer denoting further from the patient's skin. The inner layer in some embodiments contacts an external surface of an organ (e.g., skin of a breast), and the outer layer is in contact with an environment of the organ (e.g., air). A middle layer is enclosed by the inner layer and the outer layer and maintained air tight. In alternate embodiments, a layer of material, e.g., padding, forms the innermost layer to contact the skin of the patient.

The middle layer comprises one or a plurality of components configured to interlock and/or compress upon application of a negative pressure that forces them against each other to form a rigid laminate structure. For example, the middle layer may comprise beads, strips of malleable fabric, strips of cardboard, sandpaper, soft paper, thin paper, cellulose, or other woven and/or stretchable fibrous material with or without beads, strips of sponge or other porous material, or the like. It could also be composed of beads or particles suspended in a gel-like fluid whereby the application of negative pressure causes them to compact and lock together and rigidify. The components may be separate from or integral with the inner layer and/or the outer layer. Moreover, the middle layer may further include a fluid (such as air, water, or any other fluid) configured for evacuation via a port through the inner layer and/or the outer layer. The various materials of the middle layer are discussed in further detail below.

Note the middle layer can be composed of a layer of material encapsulating the one or more plurality of components configured to rigidify or alternatively the one or more plurality of components can itself constitute the middle layer (sandwiched between the inner and outer layers).

In some embodiments, when paper is used as the middle layer, thin sheets of paper such as having a thickness of about $\frac{1}{1000}$ inch can be utilized. It should be appreciated that other thicknesses are also contemplated. The at least one sheet of paper is moldable to a contour of a patient's body. In some embodiments, the sheet is smooth and devoid of irregularities on its surface. In some embodiments, the sheets of paper are crimpled, pre-wrinkled, and/or tightly folded in an accordion type design. In some embodiments, the papers are stacked with the folds in different orientations. In some embodiments the papers are cut into thin long strips oriented in multiple directions. In some embodiments the strips are woven together. In some embodiments the strips are arranged in a bird nest like configuration. In some embodiments, the at least one sheet of paper comprises a plurality of sheets of paper having a combined thickness of between about 15 mm to about 40 mm prior to rigidifying by vacuum and once rigidified, have a significantly reduced thickness. Other thicknesses are also contemplated.

The middle layer may be configured to substantially conform to an external surface of the organ before interlocking and/or compressing. Accordingly, upon aspiration (e.g., using a vacuum) of the fluid (e.g., air), the plurality of components of the middle layer interlock together and rigidify in embodiments where the components have textured or roughened surfaces or compress together to form a rigid laminate structure in embodiments utilizing smoother components such as smooth paper. Accordingly, the middle layer may be configured to espouse the surface of a swollen organ and maintain it in the expanded state after rigidifying.

In some embodiments, a sheet can be placed over the device that extends beyond its borders on the surrounding skin to maintain the vacuum seal.

Any of the rigidifying braces/stents disclosed herein may be implemented in a brassiere. For example, one or both of the cups of a brassiere for breasts can comprise the passive stents described herein. In some embodiments, additional semi-rigid frames may surround the stents and contact peripheries of the breasts. Any semi-rigid material, such as one or more polymers or the like, may be used for the frames. In some embodiments, the frame consists of a donut bladder with gel-like consistency that acts as a cushion against the skin and adhesive sole to secure an airtight seal. Additionally, or alternatively, a peripheral shirt-like extension may prevent airflow between the inner layer of the cup(s) and skin of the breasts. For example, the cup(s) may connect to fabric (whether woven, extruded, or the like) configured to conform to a torso and the breasts and block airflow between the inner layer and skin of the breasts. A sheet in the form of a donut-shape could alternatively be utilized to prevent airflow as described below in conjunction with FIG. 6A. A non-adhesive soft rubber rim that opens from convex to concave upon firm application to the body can also be used such as disclosed in commonly assigned co-pending application Ser. No. 17/534,527, filed Nov. 24, 2021, the entire contents of which are incorporated herein by reference.

According to some embodiments, a method for retaining an organ in an expanded state comprises applying at least one force to the organ to place the organ in the expanded state. To reach the iatrogenically enlarged state for example, at least one force may be applied by injecting physiologic solutions, or solutions containing growth promoting substances, or the application of vacuum, or inducing an inflammatory swelling through surgery or other means, or applying a distracting force through surface tension, or other internal or external force that induces distention in the organ. In some embodiments, the Brava Bra (see, for example, U.S. Pat. Nos. 5,536,233; 5,662,583; 5,676,634; 5,695,445; 5,701,917; 6,478,656; 6,500,112; 6,641,527; and 6,699,176, all of which are incorporated herein by reference in their entirety) and/or an external passive expander splint (see, for example, U.S. Pat. Nos. 9,066,795 and 9,522,058, also incorporated herein by reference in their entirety) may induce the distractive force and, over a period of time, place the organ in the expanded state.

The rigidifying brace of the present invention can be used to maintain the distention after distended by such device or maneuvers. Note some of these devices in the patents are utilized with fat grafting and stabilize the graft as the fat fills the void. The rigidifying braces of the present invention can be utilized after such grafting. Such grafting can include allograft or xenograft. The graft can include material derived from fat (human or animal, e.g., pig). This provides a method of augmenting tissue comprising injecting material derived from fat into a region of the body expanded by a force, e.g., a distractive force, to increase volume of the body region. The rigidifying braces disclosed herein retain the tissue in the augmented state, preserve a chronic edema state and potentiate the beneficial effect of grafts and graft tissue derived materials.

The method of the present disclosure may further comprise applying a passive stent to an external surface of the organ. For example, the passive stent may be flexible or malleable (as described above) to substantially conform to the external surface of the organ. Additionally, in some embodiments, the passive stent may be further adhered using an adhesive layer and/or a vacuum applied to a volume between the inner layer of the stent and the external surface of the organ. In some embodiments, a sheet is placed over the device to adhere to the skin and maintain a vacuum seal between the device, e.g., the inner layer, and patient's skin. An additional interposed layer between the inner layer and the skin may be provided. This layer could for example be a foam, a gel, a very low durometer rubber, or a fabric sheet that is extensible (forms no wrinkles as its surface area contracts and expands). That layer provides adhesiveness between the skin and the inner layer and has a padding buffer effect to evenly distribute the anti-deflation force upon the skin of the treated organ.

The method of the present disclosure may further comprise applying a vacuum to the passive stent sufficient to cause a plurality of components of at least one layer of the passive stent to interlock and/or compress and/or rigidify. Such application may cause surface tension between the inner layer of the stent and the external surface of the organ such that the former adheres to the latter. The surface tension may be used in lieu of or in addition to the adhesive layer and/or vacuum applied to a volume between the inner layer of the stent and the external surface of the organ described above. Accordingly, the at least one layer may be configured to maintain the organ in the expanded state after rigidifying.

In some embodiments, the disclosed devices and methods may prevent the natural tendency of distended and expanded tissues and organs to recoil without relying on curing. Accordingly, the disclosed devices and methods may be more cost-effective than existing passive braces as well as easier to implement by using a vacuum rather than ultraviolet lamps, polymerization chemicals, or other curing implements.

In some embodiments, an adhesive inner layer extends beyond the periphery of the brace to adhere the brace to the tissue and apply an airtight seal.

Referring now to the drawings and particular embodiments of the present disclosure, wherein like reference numerals identify similar structural features of the devices disclosed herein, there are illustrated several embodiments of the devices (braces) of the present disclosure. Turning first to FIG. 1, FIG. 1 is a schematic representation of brace 100 in accordance with an embodiment of the present disclosure. Brace 100 comprises an inner layer 102, an outer layer 104, and a middle layer 106 positioned between the inner layer 102 and outer layer 104. As depicted in FIG. 1, brace 100 is preferably configured to conform to an external surface of an organ, e.g., a breast.

The inner layer 102 is configured to contact an external surface (e.g., a portion of skin) of an organ (e.g., a breast) and thus is the layer closest to the patient's body. Inner layer 102 may comprise a biocompatible material, such as one or more polymers compatible with the external surface. The outer layer 104 is configured to contact the environment of the organ (e.g., the atmosphere). Outer layer 104 may comprise one or more polymers or any other material compatible with the environment.

As further depicted in FIG. 1, brace 100 preferably substantially conforms to the external surface of the organ. Therefore, inner layer 102 and outer layer 104 are composed of flexible materials, such as flexible polymers, flexible fabrics (e.g., woven or extruded fabrics), or the like. As used herein, "substantially conform" refers to contact between two surfaces containing air bubbles, obtrusions, imperfections, etc., that are sufficiently small such that one of the surfaces may still apply surface tension to the other of the surfaces. Two surfaces, then, may be termed "substantially conforming" as used herein even if not perfectly contacting each other free of air bubbles, obtrusions, imperfections, etc.

Furthermore, layers 102 and 104 are capable of increasing their surface area such that the device can conform to a relatively flat surface and also expand to conform to the much larger surface area of an expanded dome. To achieve this, in one embodiment the layers are composed of a stretchy material that can expand in two dimensions to accommodate domes of various depths; and in another embodiment the layers are composed of sheets with a large surface area that can stretch out and unfold to accommodate a deep dome and then accordion-like fold down or wrinkle to conform to a smaller dome, or even a flat surface. In some further embodiments, the layers possess both properties.

Inner layer 102 and outer layer 104 enclose a middle layer 106. Layer 106 similarly can stretch unfold and expand to accommodate various levels of dome expansion. The middle layer 106 may comprise a stretchable textured or fibrous material including fibers or beads (e.g., microbeads) configured to interlock/compress and rigidify upon application of a vacuum. For example, middle layer 106 may comprise strips of paper, such as cardboard or sandpaper, strips of sponge, strips of cellulose, or sheets of fabric amongst a fluid (e.g., air, water, an inert gel, or the like). In some embodiments, the fibrous material includes sheets of very thin paper such as smooth soft silk paper commonly used as wrapping/gift paper. Such very thin smooth soft silk paper provides the widest spectrum from soft and fully malleable to wood hard rigid at the lowest vacuum pressure and the least thickness. Thus, such paper advantageously goes from super soft (for moldability to the contour of the patient's body to super hard). The soft paper has an advantage over certain other materials, such as sandpaper, which can in certain applications be too stiff/rigid. Also, such soft paper has the advantage of being super thin so that it is more concealable, especially important when the brace is used as a brassiere for breast augmentation. In some embodiments, instead of sheets, the paper-like material is comprised of strips tethered at the periphery on one end and free to interweave in various directions along the other free end. Each sheet of paper can have a thickness of about $\frac{1}{1000}$ inch, although other thicknesses are also contemplated. In some embodiments, the sheet is smooth and devoid of irregularities on its surface and thus rather than interlocking as in embodiments with components having irregular or textured surfaces, it compresses together to form a rigid laminate structure. In some embodiments, the at least one sheet of paper comprises a plurality of sheets (layers) of paper having a combined thickness of between about 15 mm to about 40 mm prior to rigidifying by vacuum and once rigidified, have a significantly reduced overall thickness. In some embodiments by way of example, 8-10 sheets of could be provided, although a different number or sheets is also contemplated. The sheets or strips can be fixed at only one point or region so they can slide. Stated another way, the sheets can be held on one side while the other end is free so they can slide past one another and overlay to stretch out as the dome spreads (stretches from a plane to a dome). Thus, the sheets can rigidify within the dome as it changes in size and its surface area increases as it goes from a more flattened configuration (a plane) to increased size dome (hemispherical) configuration as the height increases. This increase is multi-dimensional—in at least two planes.

Note that the rigidifying process of the present disclosure is reversible so that the components of the middle layer can return to their softer form by changing the pressure within the middle layer.

Use of such soft paper in some embodiments has an advantage over beads which, unless tethered or restrained by some stretchable fabric, have a tendency to fall to the bottom of the layer. The paper provides a more uniform distribution.

Additionally or alternatively, the middle layer may comprise a foamy or porous material configured to interlock and rigidify upon application of a vacuum. For example, middle layer 106 may comprise textured polyurethane, textured polybutene, plastic or Styrofoam beads, or the like amongst a fluid (e.g., air, water, an inert gel, or the like).

In some embodiments, the interlocking materials in the middle layer 106 may be structurally part of the inner layer 102 and/or structurally part of the outer layer 104. In other embodiments, they are independent, i.e., not structurally part of, the middle layer or outer layer. In some embodiments, as discussed above, inner layer 102 and outer layer 104 may enclose a fluid (e.g., air, water, an inert gel, or the like). Aspiration of that fluid, e.g., through a syringe or a pump, whether mechanical or manual, collapses the middle layer 106. In general, air aspiration, extraction of a gel or fluid in the middle layer, electromechanical mechanisms such as interlocking magnets or a Velcro-like mechanism, or any other appropriate mechanism may cause the materials in the middle layer 106 to connect together and rigidify.

Collapse of middle layer 106 may result in the interlocking of the structures comprising middle layer 106. For example, as explained above, the middle layer 106 may comprise textured foam, textured putty, and/or gel with fibers and/or beads configured to interlock and become rigid when a radial thickness of the same is forcefully reduced, e.g., by vacuum or aspiration of fluid in middle layer 106. Additionally or alternatively, interlocking/compressible structures of the middle layer 106 may comprise sheets of paper, malleable fabric, or other malleable material configured to become stiff when pressed together, e.g., by forceful removal of air, water, or other ambient fluid in middle layer 106. The expelled fluid may comprise air or another gas such that removal results in a vacuum or may comprise an inert liquid or gel such that removal forces the components of middle layer 106 to interlock and/or compress together such that the components collectively stiffen.

In some embodiments, the middle layer may have a variable thickness. The variable thickness may improve the adaptability of the middle layer to morphology of the external surface of the organ. For example, the middle layer 106 may comprise polymer foam, e.g., polyurethane or polybutene, having a thickness adjusted by aspiration of air contained therein. Through a controlled reduction of its volume and thickness, e.g., using a vacuum as described above, the middle layer 106 may substantially conform to the morphology of the organ, and the textured foam, fibers, beads, or the like of middle layer 106 may interlock to rigidify and prevent the external surface from recoiling. By counteracting recoil forces, the device may also passively impart a distractive force to the organ.

Figure 2:
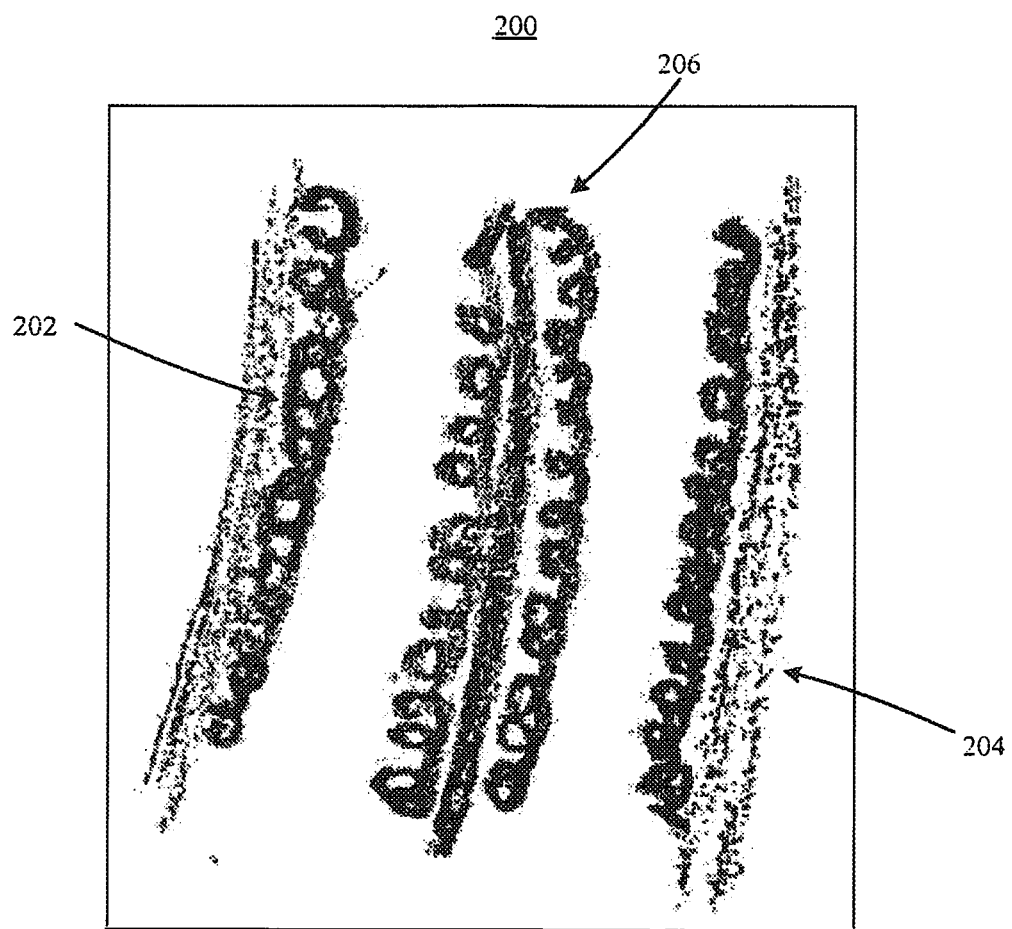
FIG. 2 is a schematic representation of a middle layer of the rigidifying brace of FIG. 1.

FIG. 2 is a schematic representation of a zoomed-in version of exemplary brace 200. For example, brace 100 of FIG. 1 may comprise brace 200 of FIG. 2. As shown in FIG. 2, inner layer 202 of the brace may include textured or rough material and/or ridges, whether random or in a pattern, at least on a portion of inner layer 202 facing middle layer 206. Similarly, outer layer 204 may include textured or rough material and/or ridges, whether random or in a pattern, at least on a portion of outer layer 204 facing middle layer 206.

As further depicted in FIG. 2, middle layer 206 may comprise stacked layers of fibers, strips of paper, sheets of fabric, and/or restrained beads. For example, the fibers may comprise inter-digitating layers, fibers, strips, sheets and/or beads, whether random or in a pattern.

Figure 3A:
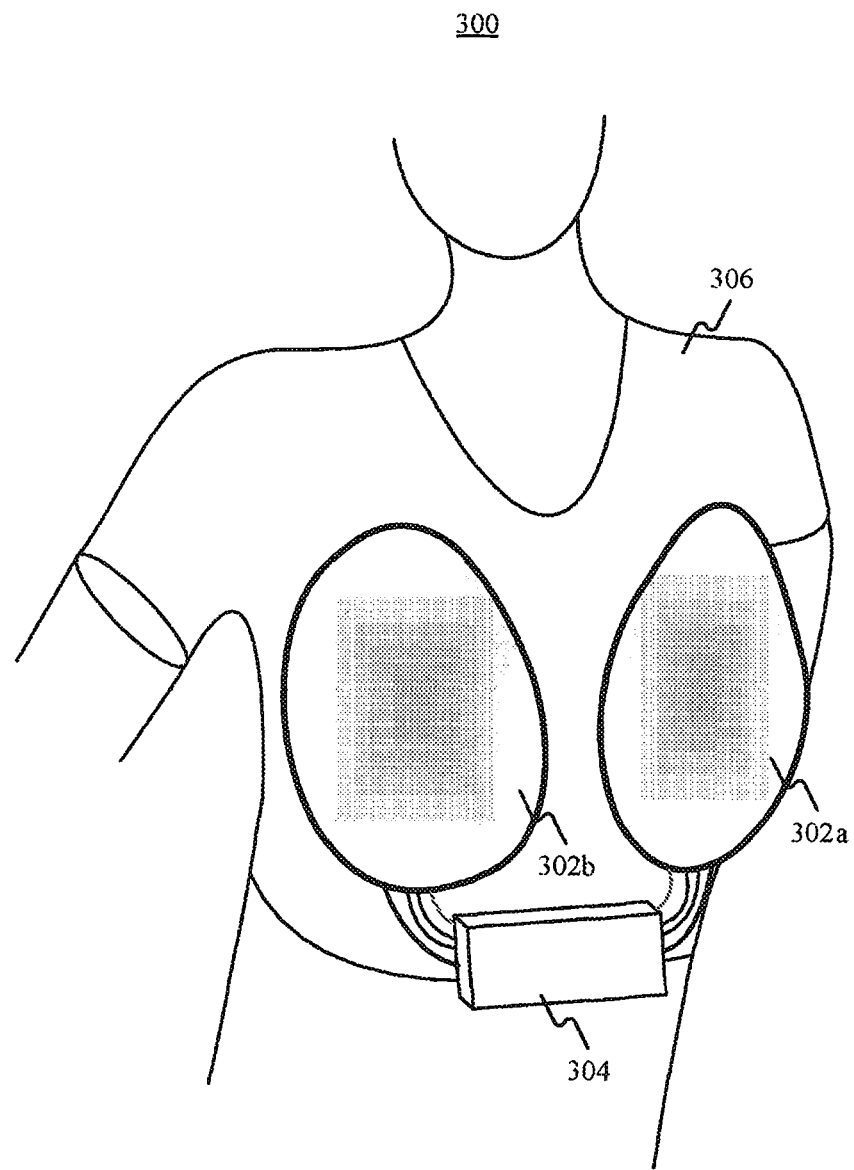
FIG. 3A is a schematic representation of a brassiere incorporating the rigidifying brace of FIG. 1.
Figure 3B:
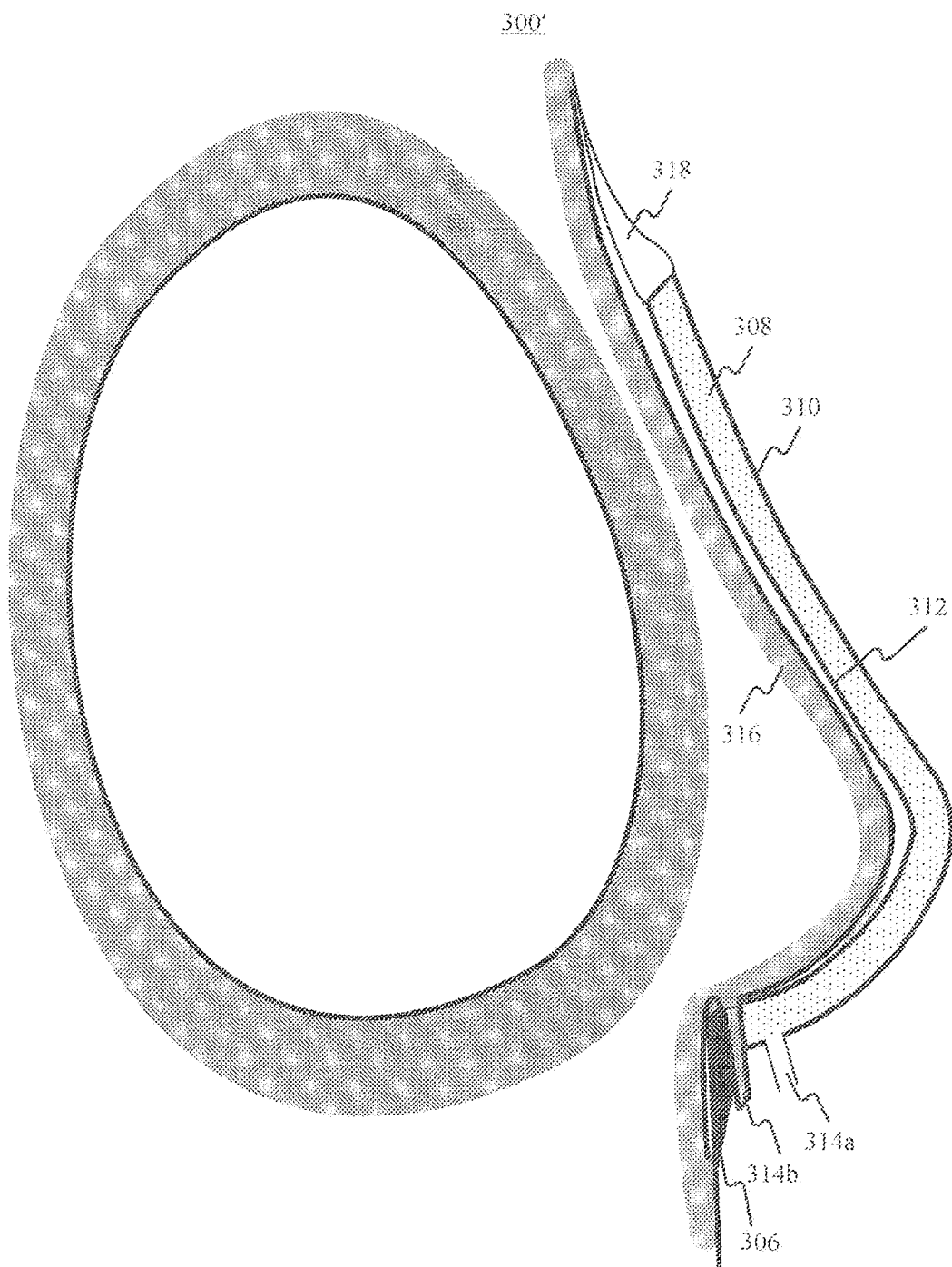
FIGS. 3B and 3C are side views of the brassiere of FIG. 3A incorporating the rigidifying brace of FIG. 1.
Figure 3C:
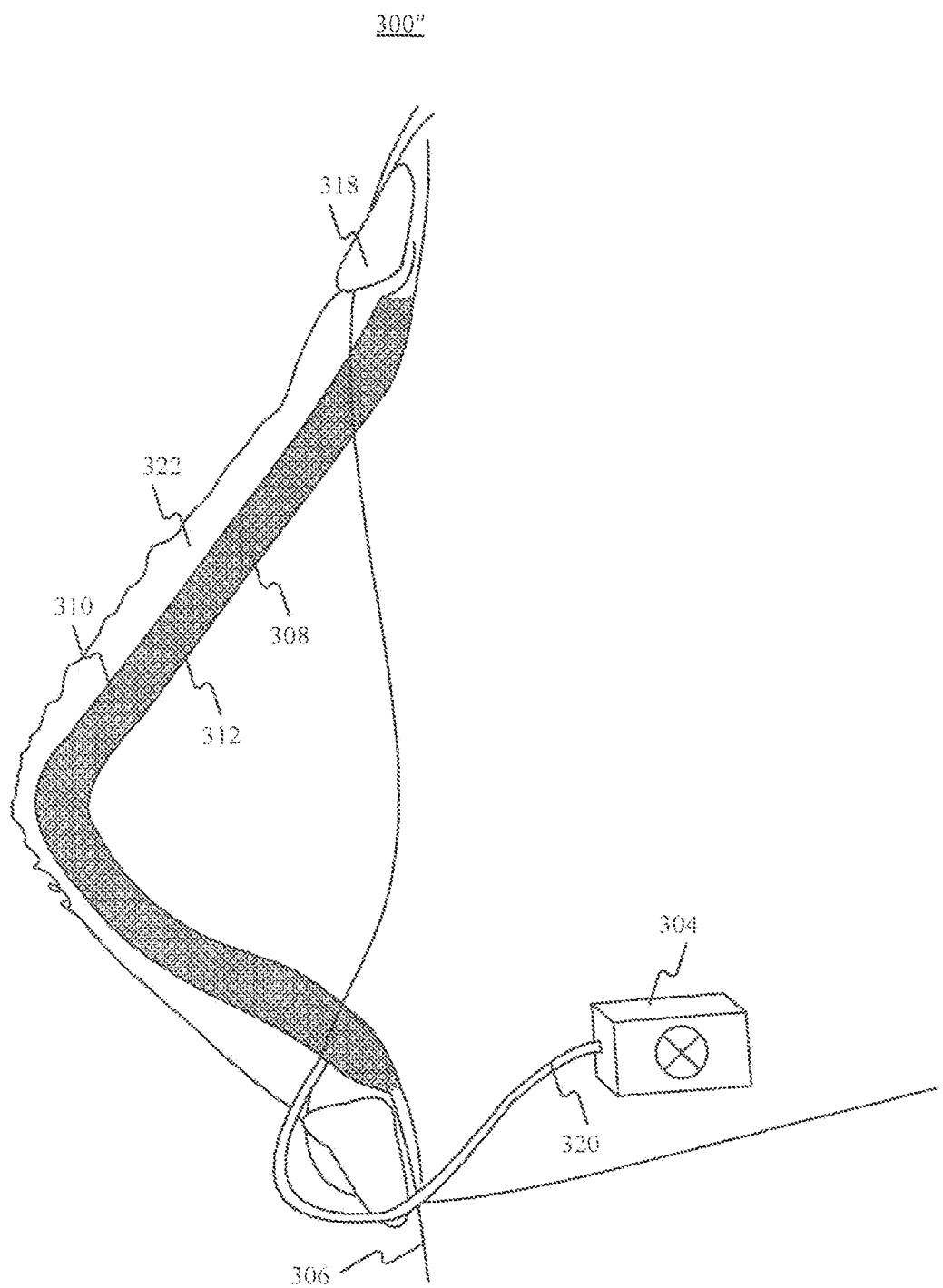

The devices of the present disclosure can be used in various parts of the body. The devices can be used in tissue expansion/augmentation procedures utilizing vacuum expansion. In one embodiment, the device in used as a brassiere. FIG. 3A is a schematic representation of an exemplary brassiere 300 incorporating a rigidifying brace, such as brace 100 of FIG. 1 and thus has a middle rigidifying layer between the inner and outer layers. Brassiere 300 may be taken on and off by an individual (e.g., as depicted in FIGS. 3B-3D described below). One or both cups 302a and 302b of the brassiere 300, depending on its intended use, comprise a passive stent as described herein (e.g., stent 100 of FIG. 1 with an inner layer, an outer layer and a stiffening middle layer). The cup(s) 302a, 302b are preferably composed of a stretchable material, such as a sheet of fabric (whether woven, extruded, or the like) or other polymer, configured to conform to the morphology of the breasts. Upon forceful expulsion of fluid (such as air, water, or the like) from the middle layer of the stent of each cup 302a 302b as described above, the cup(s) 302a, 302b rigidify and maintain the shapes and corresponding volumes of the breasts. Moreover, the inner layers of the stents may adhere to the surface of the breasts, whether from surface tension between the inner layers and the skin of the breasts, suction from a vacuum applied to a volume between the inner layers and the skin of the breasts, a medical grade adhesive (for adhesive layer) between the inner layers and the skin of the breasts (e.g., as depicted in FIG. 3B and described below), or a combination thereof.

As further depicted in FIG. 3A, the brassiere 300 may include a control mechanism 304 worn by the user. The control mechanism 304 may include, for example, a) one or more vacuum pumps to activate the middle layer as described herein and/or b) controls for monitoring and correction of airflow between the inner layers and the skin of the breasts as described below with respect to method 500 of FIG. 5), and/or c) controls for monitoring and correction of vacuum to the middle layer, and/or d) one or more pressure sensors (e.g., for monitoring airflow between the inner layers and the skin of the breasts as described below with respect to method 500 of FIG. 5), and/or e) an energy source (e.g., a battery, fuel cell, or the like) for powering the pump(s) and/or sensor(s), and/or f) a servo control mechanism (e.g., a microprocessor for generating commands and/or a communications interface for receiving commands) for the pump(s) and/or sensor(s). Furthermore, the level of pressure in each of the individual chambers (the middle layer chamber and the skin to inner layer chamber) can be monitored and adjusted as required for the particular conditions.

Moreover, in some embodiments, brassiere 300 may further comprise an extension 306. The extension 306 may comprise fabric or other polymer. As shown in FIG. 3A, extension 306 surrounds, at least in part, a torso of which the breasts are part. Accordingly, extension 306 may comprise a shirt-like garment to which cups 302a and 302b are attached (e.g., via sewing, weaving, adhesive, or the like). Extension 306 may secure cups 302a and 302b to the torso and/or may prevent airflow between the inner layers of the stents comprising the cups and skin of the breasts, thus enhancing a vacuum seal between the inner layer and breasts. The extension 306 can be an extension of the outer layer and/or the inner layer.

FIGS. 3B and 3C are side views 300' and 300", respectively, of brassiere 300 of FIG. 3A. FIG. 3B further depicts a semi-rigid frame 318 that defines peripheries of cups 302a and 302b. Frame 318 may further bear counterforces on cups 302a and 302b from the breasts and hold active components of cups 302a and 302b (e.g., inner layers and middle layers of stents of cups 302a and 302b) in place against the skin of the breasts. In such embodiments, extension 306 may attach to frame 318 (e.g., via sewing, weaving, adhesive, or the like), which is then attached to cups 302a and 302b (e.g., via sewing, weaving, adhesive, or the like).

Inner layer 312 of cups 302a and 302b may contain textured or rough material and/or ridges, whether random or in a pattern as explained above with respect to FIG. 2 and outer layer 310 of cups 302a and 302b may contain textured or rough material and/or ridges, whether random or in a pattern as explained above with respect to FIG. 2. The surface area of the inner layer and the outer layer are capable of changing in order to accommodate the changes in the breast size. The middle layer 308 of cups 302a and 302b comprise one or more components which rigidify via application of vacuum, such as stacked layers of fibers, strips or sheets of paper, sheets of fabric, and/or restrained beads, such as inter-digitating layers, fibers, strips, sheets and/or beads, whether random or in a pattern, as explained above with respect to FIG. 2 and any other materials as described herein.

Layer 316 of brace 300 adheres to the skin with tissue glue, pressure sensitive adhesive, and/or other types of biocompatible glue. Furthermore, layer 316 can also stretch to accommodate changes in breast size and this layer plays an important role in buffering the potentially skin damaging effects of wrinkles and surface irregularities of the inner layer 312. To this effect, layer 316 can be a gel or a very low durometer rubber (which can have intrinsic adhesive properties), or a conforming stretchable sponge-like or felt-like material or relatively thick cotton or fabric material that is either adhesive on both sides or porous such that it can transmit the vacuum-induced adhesion between skin and inner layer, and or consists of a fluid that would best transmit an even isotropic counterforce to the skin, or some combination of the above alternatives.

Layer 316 can also be applied separately first over the breast as a conforming brassiere with the above properties prior to application of the remainder of the device. Some embodiments may omit adhesive layer 316. Such embodiments may use surface tension between the inner layer 312 and the skin of the breast arising after interlocking of the components of middle layer 308 to achieve adherence. Additionally or alternatively, such embodiments may cause adhesion between the inner layer 312 and the skin of the breast by aspirating air in a volume between the inner layer 312 and the skin of the breast and/or by allowing the inner layer 312 to be porous and/or have fine holes such that the vacuum created in the middle layer 308 also adheres the skin of the breasts to the inner layer 312.

Brassiere 300' further includes tubing 314a extending through outer layer 310 and into middle layer 308 to apply a vacuum to middle layer 308 such that the components of middle layer 308 interlock. In some embodiments, the tubing 314a can extend through the inner layer 312 and into the middle layer 308; in other embodiments, the tubing can extend directly into the middle layer 308. In some embodiments, such as brassiere 300', tubing 314b extends through inner layer 312 configured to apply a vacuum to a volume between the inner layer 312 and the skin of the breast (as described above). The tubing extending into the middle layer in the various embodiments disclosed herein can have a non-linear configuration, such as one or more curves, e.g., an S-shape, and have multiple perforations for application of vacuum. Such tubing can be used with other braces disclosed herein.

Brassiere 300' includes a frame 318 and extension 306, described above with respect to FIG. 3B. In the embodiment of FIG. 3C, brassiere 300" has additional fabric (whether woven, extruded, or the like) or other polymers to cover cups 302a and 302b in layer 322. Layer 322 may improve fashionability of brassiere 300". FIG. 3C also depicts control mechanism 304 as described above with respect to FIG. 3A. Such control mechanism 304 can be used with brassiere 300' of FIG. 3A as well as with the other braces disclosed herein. In brassiere 300", control mechanism 304 applies a vacuum to middle layer 308 using tubing 320 through outer layer 310, although in other embodiments, tubing 320 may proceed through inner layer 312 or go directly into the middle layer 308. Accordingly, the vacuum applied to middle layer 308 may enter through one or more ports passing through inner layer 312 and/or outer layer 310 or directly into the middle layer. Similarly, any vacuum applied to a volume between the inner layer 312 and the skin of the breast may enter through one or more ports passing through inner layer 304 (optionally with outer layer 310 as well) and/or frame 310.

Figure 6A:
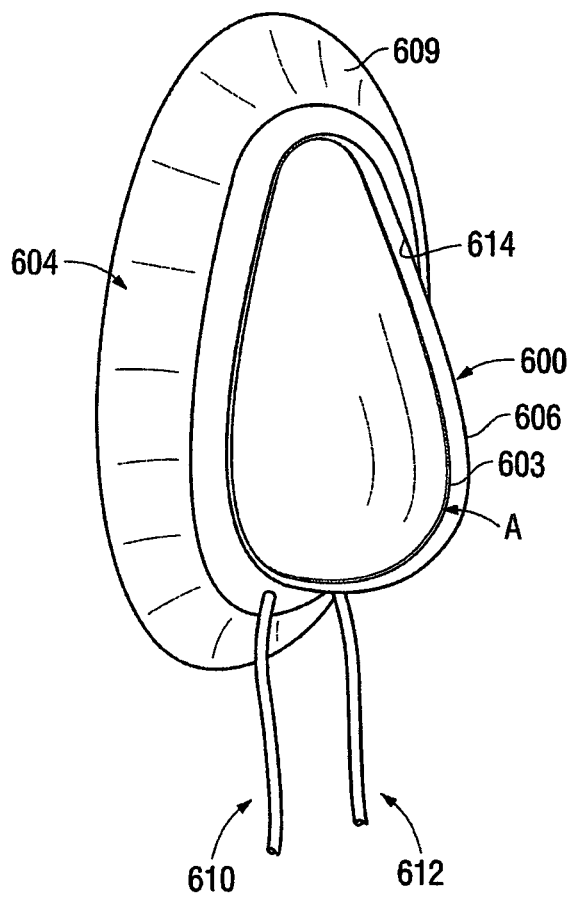
FIG. 6A is a schematic representation of an alternate embodiment of a rigidifying brace of the present disclosure having an adhesive sheet attached to the rim of the brace.
Figure 6B:
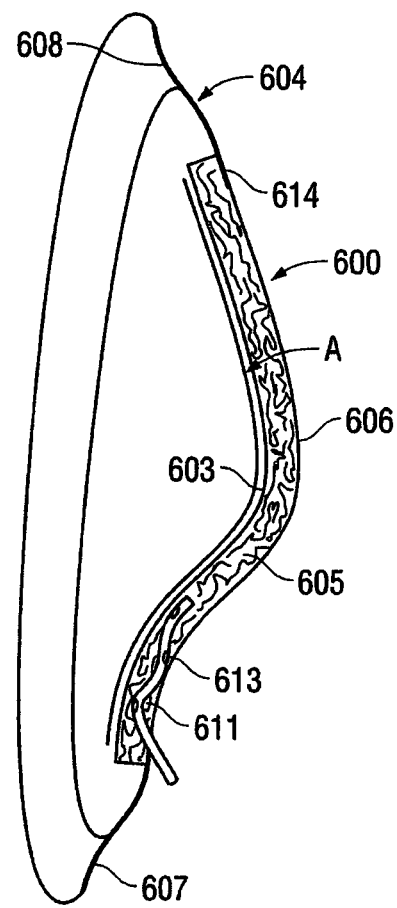
FIG. 6B is a schematic representation of the brace of FIG. 6A.

To reduce occlusion (blockage) of the vacuum, a S-shaped tubing 611 (or other non-linear shapes) having a plurality of openings/perforations 613 can extend from the port into the middle layer as shown in FIG. 6B. Blockage is reduced since if one of the openings is blocked, vacuum can still be applied to the remaining open openings.

Figure 8:
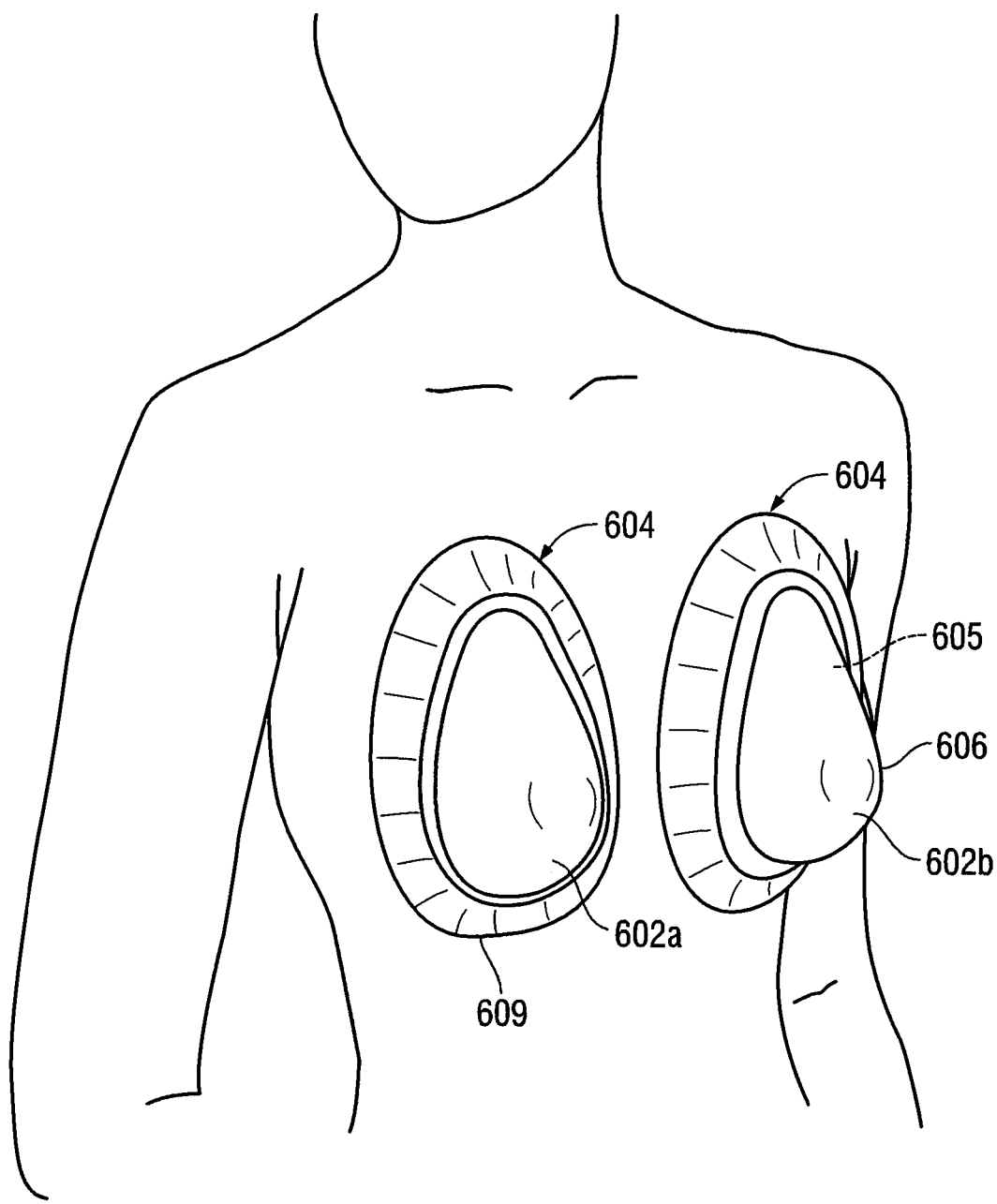
FIG. 8 is a perspective view of the rigidifying brace of FIG. 6 placed over the breasts of an individual and shown held up by concave soft rubber rim that becomes convex upon espousing the contour of the torso to preserve an adhesive seal of the brace to skin.

In an alternate embodiment of FIGS. 6A, 6B and 8, brace 600 is in the form of a brassiere and has a pair of cups 602a, 602b (collectively referred to as cups 602) for placement over each breast in the same manner as cups 302a, 302b. (In alternate embodiments, a single cup/brace could be provided). Brace 600 has an inner layer 603 adjacent the breast skin A, an outer layer 606, a middle layer 605 between the inner and outer layers 603, 606, and a thin sheet 604 which is placed over a section of the outer layer 606 and extends beyond a periphery of the outer layer 606. The middle layer 605 includes one or more of the components/material described above sandwiched inside the outer and inner airtight layers (e.g., sheets). Sheet (cover) 604 has an outer surface 607 and an inner surface 608. The inner surface 608 has an adhesive surface covered by a peel away strip. The adhesive surface extends around a periphery of the sheet 604. The sheet 604 includes an opening that is preferably configured so that the majority of the brace 600 is exposed when placed thereover, except for the peripheral rim 614 of brace 600. The sheet 604 is placed over the brace 600 so that the adhesive rim 609 of the sheet 604 adhesively attaches to rim 614 of the outer layer 606 of brace 600 and extends beyond the confines of the brace 600, i.e., laterally beyond the rim 614, preferably extending around the entire circumference of the brace 600, to also adhesively attach to skin A. Note the peel away strip is removed prior to attachment so that the sheet 604 can adhere to the rim 614 of the brace 600 and to the patient's skin. As can be appreciated, such adherence is outside the area in which the inner layer 603 contacts the skin of the patient. In this manner, any adhesive is outside the area of vacuum applied between the inner layer 603 and skin A. This reduces damage to the skin which can occur if vacuum is applied to a region where the inner layer is adhesively attached. As shown in FIGS. 6A, 6B and 8, the sheet 604 is donut-shaped, but other shapes can be utilized. Thus, the donut-shaped sheet 604 is adherent to the rim 614 of the conforming brace 600 and the surrounding skin to maintain a vacuum seal.

The braces of the brassiere 600 held by adhesive sheets is shown in FIG. 8. As depicted, a sheet 604, preferably donut-like in shape, extends over each cup 602, beyond the periphery of cups 602 and around an entire circumference of each cup 602. The sheet 604 can be removable and replaceable with another sheet 604.

It should be appreciated that the discussion throughout this application of the various brassieres is applicable to a brassiere having one cup (one rigidifying brace) or two cups (two rigidifying braces). Thus, the present invention encompasses a one cup or two cup brassiere.

Brace 600 includes a vacuum port 610 for applying vacuum to adhere the skin to the inner side of the brace. Vacuum port 612 communicates with the middle layer 605 to rigidify the middle layer, and as noted above, the port can enter directly into the middle layer 605 or communicate with the middle layer by initial entry through the outer layer 606 or inner layer 603. A tubing 611 with a plurality of perforations 613 as described herein can communicate with the vacuum port 612 and can have one or multiple curves, e.g., have an S-shape.

Note FIG. 6 shows the brace 600 containing multiple layers of the thin paper, e.g., gift wrap paper, or strips of newspaper material sandwiched inside the two airtight sealed layers/sheets. It should be appreciated that the sheet 604 could also be utilized with braces having middle layers containing one or more components/material other than the thin paper-like material such as the various component/materials of the middle layer disclosed herein. To be very malleable, the thin paper-like material need not be porous or have a rough surface as the friction caused by the strong compressive effect might be enough to prevent the individual components from sliding past each other and become a rigid laminate.

Figure 7:
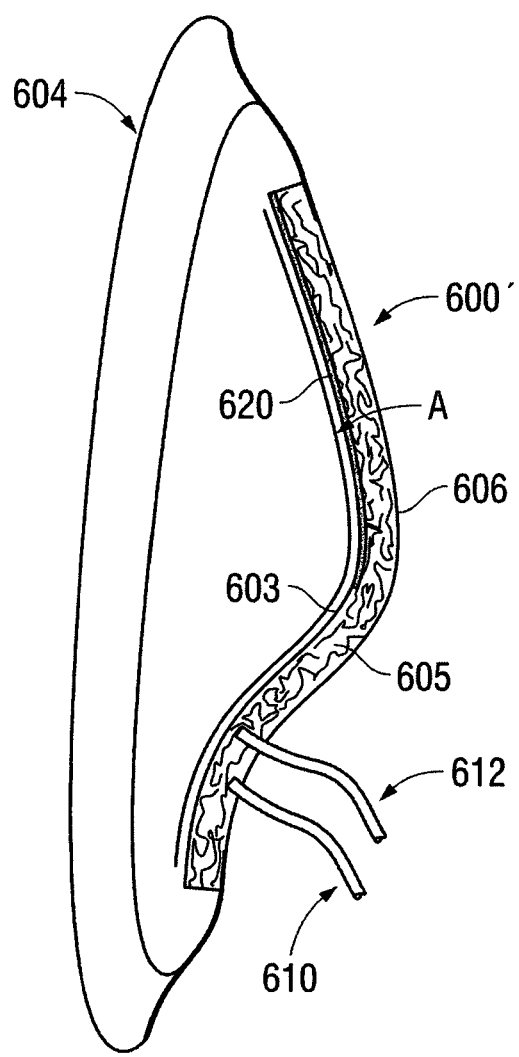
FIG. 7 is a schematic representation of an alternate embodiment of a rigidifying brace of the present disclosure having an adhesive sheet attached to the rim of the brace and a layer of padding to smooth out brace wrinkles effect on the skin surface.

To smooth out the brace and reduce the wrinkle effect on the skin surface, a layer of padding can be placed on the inner layer, interposed between the inner layer and skin. In this version, the inner layer does not directly contact the skin as the padding provides a buffering layer that contacts the skin. Such padding is shown in the embodiment of FIG. 7 wherein brace 600' is identical to brace 600 of FIG. 6 except for padding 620. Therefore, the parts of brace 600' are shown with the same reference numerals as brace 600, e.g., inner layer 603, outer layer 606, middle layer 605 sheet 604, etc., as the components and function are the same except for padding 620' attached to an inner surface of inner layer 603. As described above, that padding layer could be a gel or low durometer material that can stretch and that is also adhesive, a stretchable foam, felt, or sponge, or a stretchable fabric that adheres to both the skin and the inner layer and cushions the potential irregular contours of the inner layer and prevent pressure points against the skin. It could also be porous to transmit the vacuum adhesion effect.

Figure 4A:
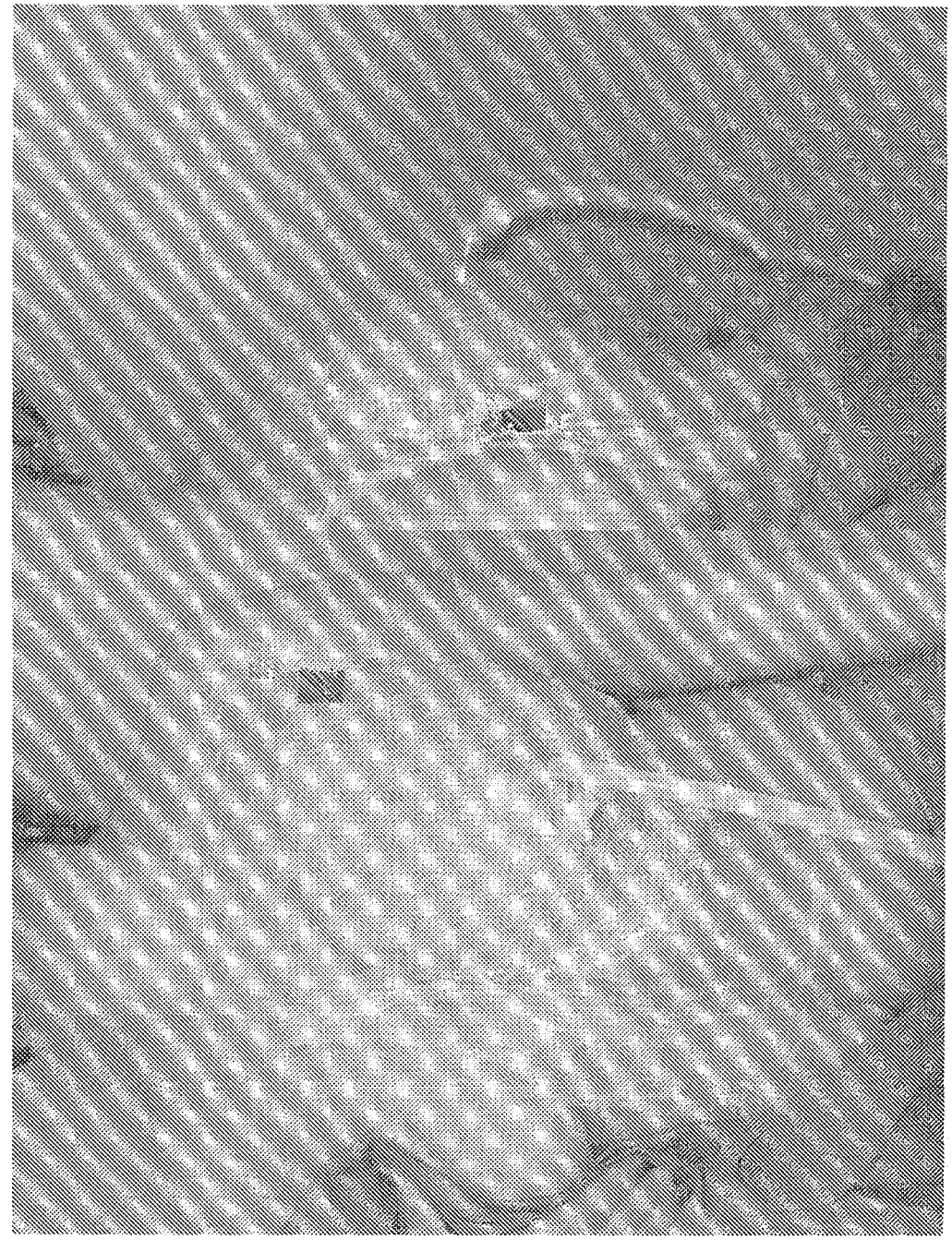
FIGS. 4A, 4B, 4C, 4D, 4E, 4F, and 4G are pictures of one implementation of the exemplary brassiere of FIG. 3A, according to the present disclosure.

FIG. 4A is an image of an exemplary implementation 400 of a brassiere (such as brassiere 300 of FIG. 3) incorporating a rigidifying brace, such as brace 100 of FIG. 1. FIG. 4A includes a vacuum connected via a port through the outer layer and into the middle layer of the brassiere to rigidify the middle layer of the stents within the cups of the brassiere.

Figure 4B:
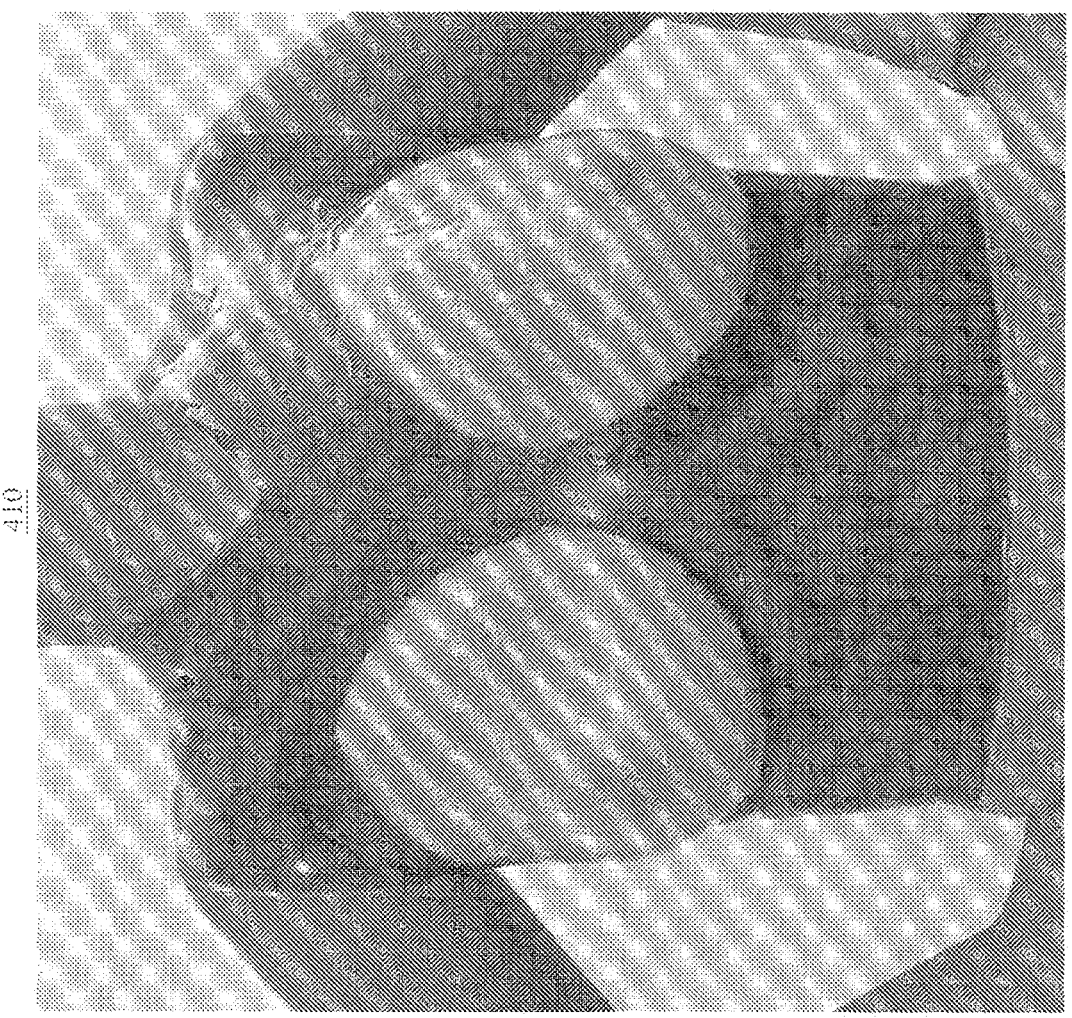
Figure 4C:
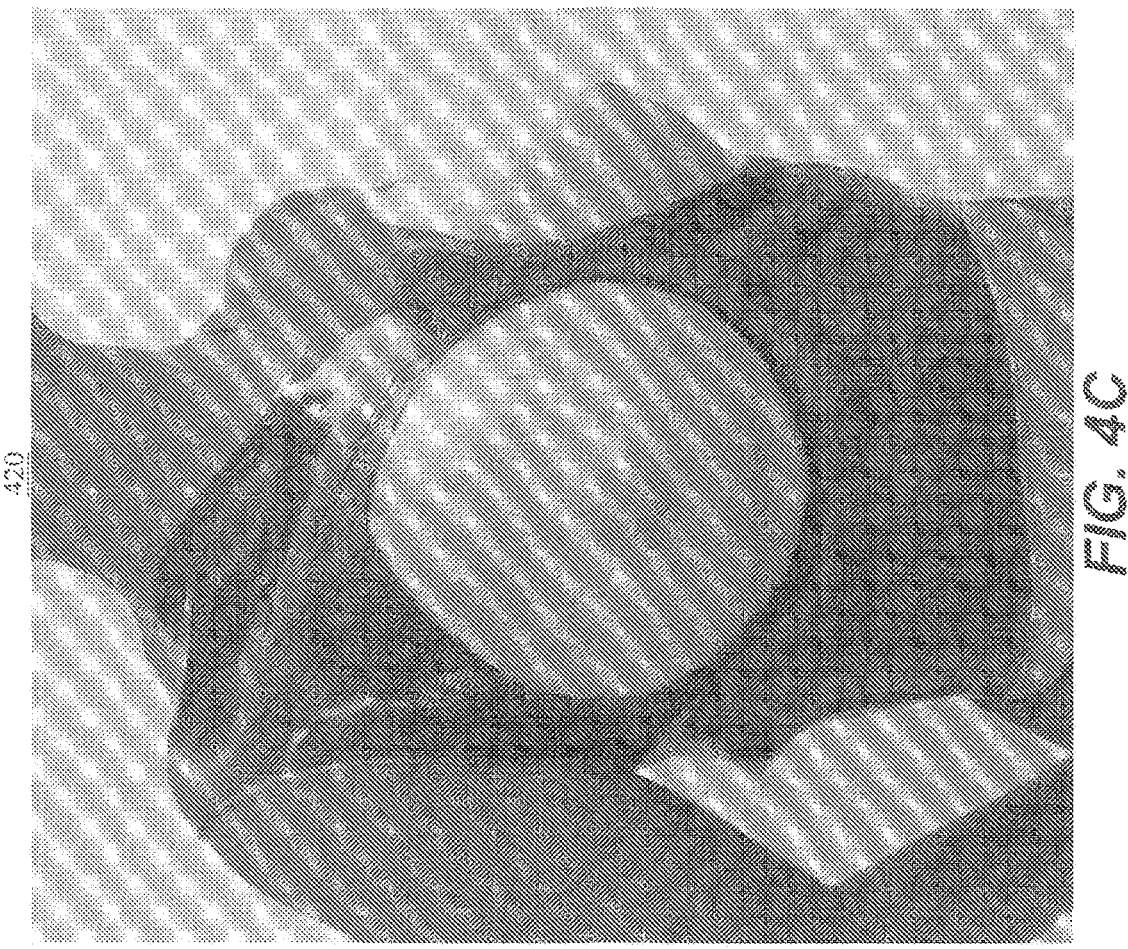
Figure 4D:
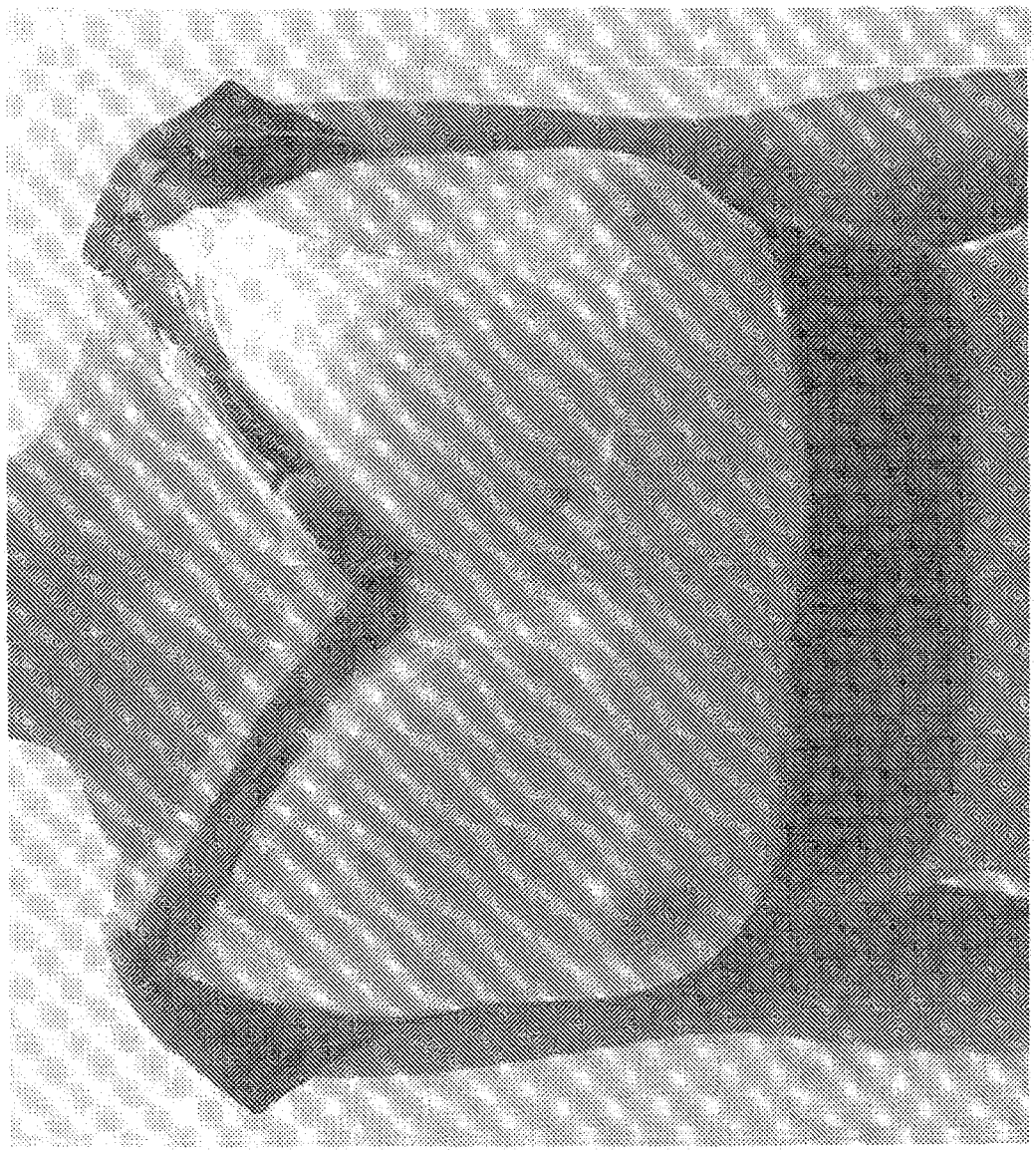

FIGS. 4B, 4C, and 4D are further images of exemplary implementations 410, 420, and 430, respectively, of a brassiere (such as brassiere 300 of FIG. 3) incorporating a rigidifying brace, such as brace 100 of FIG. 1. As shown in implementations 410, 420, and 430 of FIGS. 4B, 4C, and 4D, respectively, the brassiere may include a peripheral shirt-like extension (e.g., comprising a fabric, whether woven, extruded, or the like, or any other polymer or compatible material) that conforms to the torso and is configured to prevent airflow between the inner surface (inner layer) of the cups and the skin of the breasts.

Figure 4E:
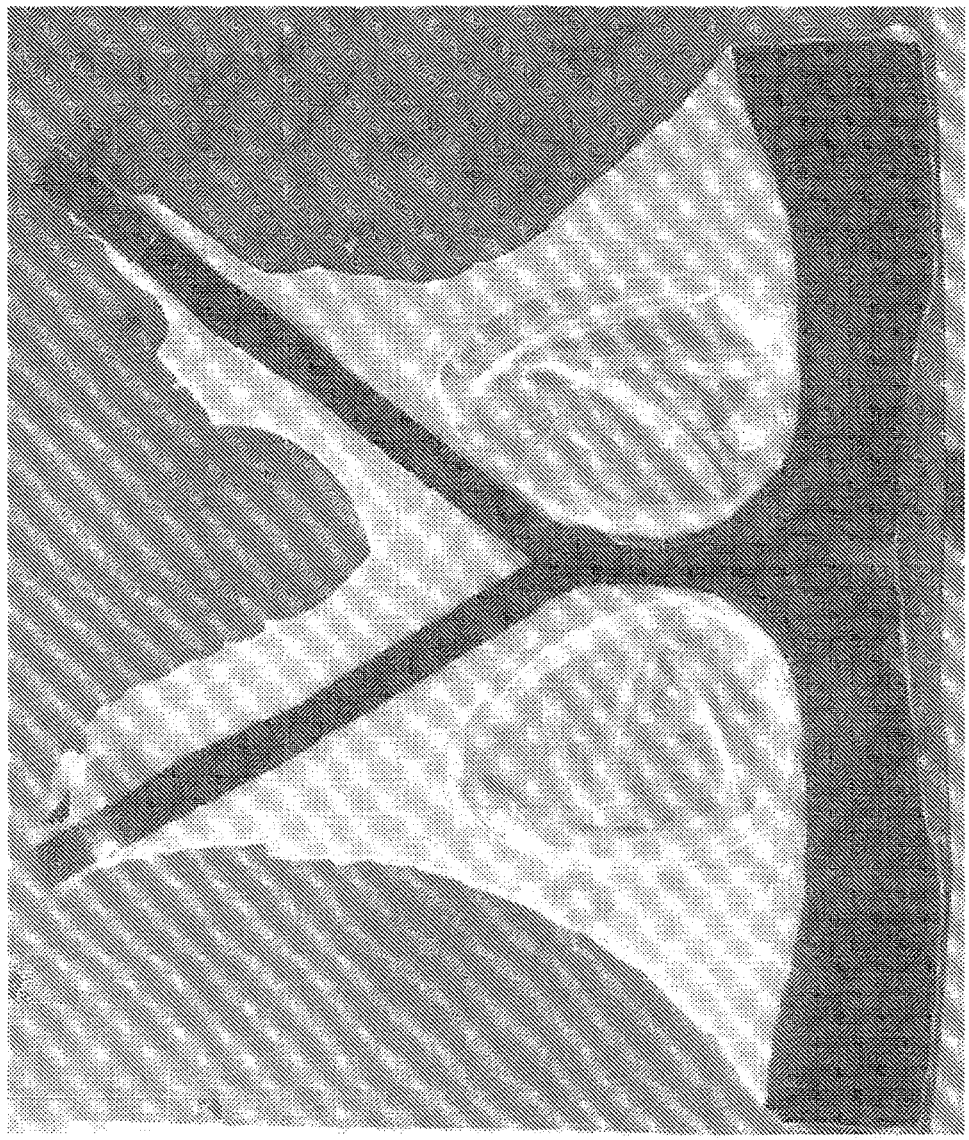

FIG. 4E is a further image of an exemplary implementation 440 of a brassiere (such as brassiere 300 of FIG. 3) incorporating a rigidifying brace, such as brace 100 of FIG. 1, but placed on a table rather than on a body of an individual as depicted in implementations 410, 420, and 430 of FIGS. 4B, 4C, and 4D, respectively.

Figure 4F:

FIG. 4F is an image of an exemplary implementation 450 of a brassiere (such as brassiere 300 of FIG. 3) incorporating a rigidifying brace, such as brace 100 of FIG. 1 using surface tension to adhere to an external surface of a breast. As shown in FIG. 4F, adhesion between the inner layer and the skin of the breast is achieved via surface tension. For example, a thin layer of fluid with high surface tension coefficient, such as water, can provide sufficient adhesive force. Surface tension may adhere while allowing the tissues of the breast to glide and thus avoid potential shear forces. Surface tension also may reduce a need for any adhesive substance that might irritate the skin of the breast. Furthermore, surface tension may be reapplied as described below with respect to method 500 of FIG. 5.

Additionally or alternatively, the cups may adhere to the breasts by using a vacuum, such as by aspirating air between the inner layer and the skin of the breasts and/or by allowing the inner layer to be porous and/or have fine holes such that the vacuum created in the middle layer of the cups also adheres the skin of the breasts to the inner layer.

Additionally or alternatively, the inner layer may adhere to the skin using a pressure sensitive adhesive and/or other types of glue. In such embodiments, the inner layer may be impermeable to the air or fluid in the middle layer.

Figure 4G:
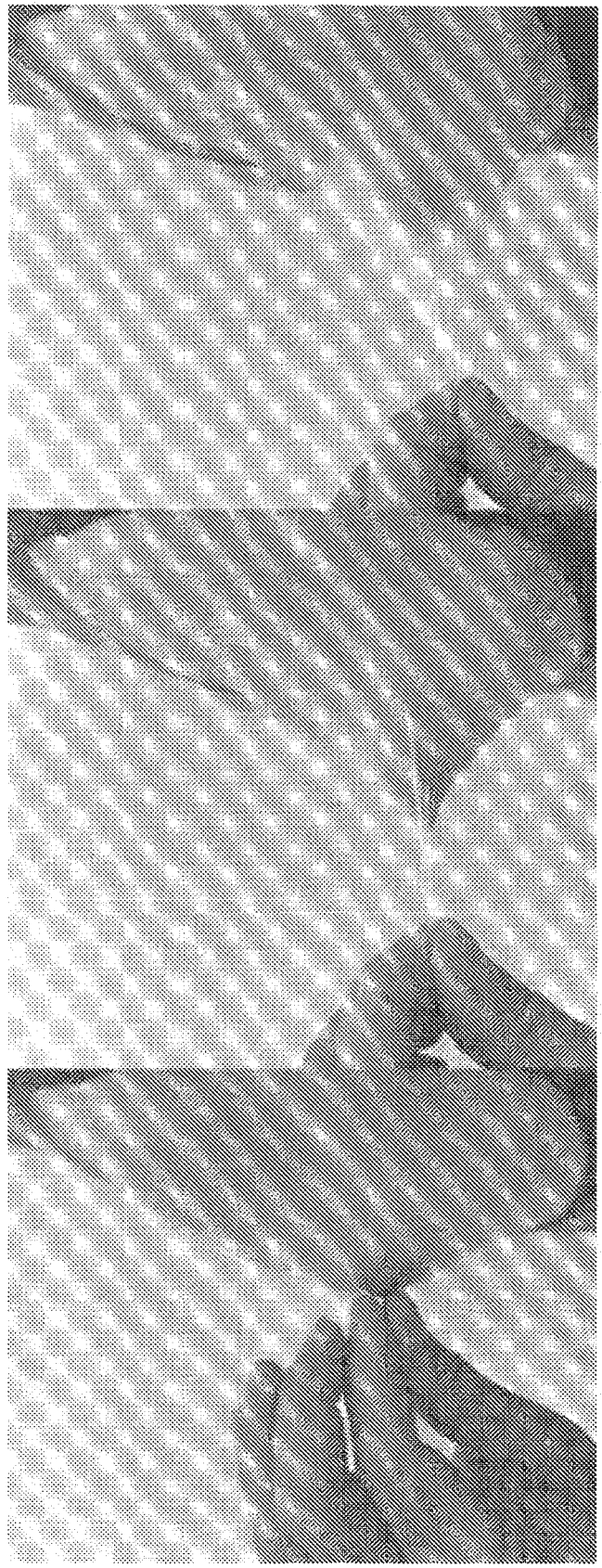

FIG. 4G is an image of an exemplary implementation 460 of a brassiere (such as brassiere 300 of FIG. 3) incorporating a rigidifying brace, such as brace 100 of FIG. 1 showing airflow between the inner layer of the brace and the external surface of the breast. As shown in the example of FIG. 4G, airflow between the inner layer of the brace and the external surface of the breast may cause a reduction in, or even loss of, surface tension between the brassiere and the breast. Embodiments using an adhesive layer (e.g., as shown in FIG. 3B) may retain adhesion even in the event of such airflow. Moreover, as described below with respect to method 500 of FIG. 5, a sensor may monitor air pressure between the inner layer of the brace and the external surface of the breast to allow for remedial measures to be taken if airflow, like that shown in FIG. 4G, causes a reduction in, or even loss of, surface tension.

Figure 5:
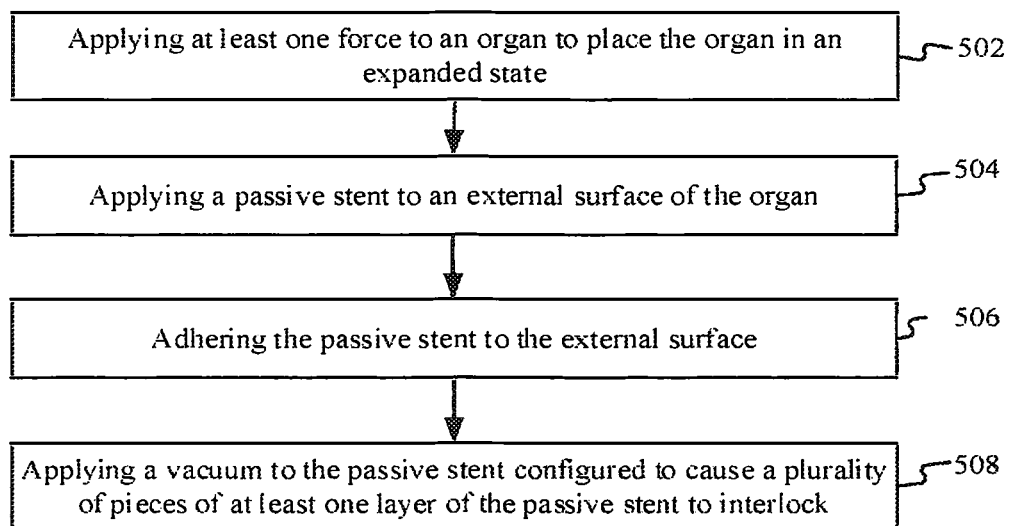
FIG. 5 is a flowchart of one method of the present disclosure for retaining an organ in an expanded state.

FIG. 5 is a flowchart of an exemplary method 500 for retaining an organ in an expanded state. Method 500 may be performed using the rigidifying brace 100 as depicted in FIG. 1 or other braces disclosed herein. Method 500 may also be performed using any of the brassieres disclosed above (e.g., as shown in FIGS. 3A-3C or 6A-8).

At step 502, at least one force is applied to the organ to place the organ in the expanded state. For example, a physiologic solution may be injected in the desired area. The physiologic solution may comprise a vasoconstrictive agent. In some embodiments, the physiologic solution may further comprise an anesthetic, a bonding agent, and/or a rejuvenating agent. In some embodiments, the physiologic solution may comprise a sclerosing agent, e.g., Doxycycline, and/or a tissue glue. In some embodiments, the physiologic solution may be injected via an infusion catheter. In some embodiments, the physiologic solution may be distributed evenly over the area, for example, by moving the catheter during injection.

Additionally or alternatively, a distractive force may be applied to the organ. For example, a vacuum, surface tension, or other external force may induce distention in the organ. In some embodiments, the Brava Bra (see, for example, U.S. Pat. Nos. 5,536,233; 5,662,583; 5,676,634; 5,695,445; 5,701,917; 6,478,656; 6,500,112; 6,641,527; and 6,699,176, all of which are incorporated herein by reference) and/or an external passive expander splint (see, for example, U.S. Pat. Nos. 9,066,795 and 9,522,058) may induce the distractive force and, over a period of time, place the organ in the expanded state.

At step 504, a passive stent is applied to an external surface of the organ. For example, the passive stent may comprise an inner layer in contact with the external surface of the organ, an outer layer opposite the inner layer, and a middle layer between the inner layer and the outer layer, as described above and depicted in FIGS. 1 and 2 and 6A-8. Accordingly, the passive stent may be configured to substantially conform to the external surface before the middle layer of the same undergoes interlocking/compression/rigidifying.

At step 506, the passive stent is adhered to the external surface. For example, an adhesive, such as tissue glue, may be applied between the inner layer of the stent and the external surface of the organ, as depicted for example in FIG. 3B or an adhesive donut sheet as in FIG. 6A.

In some embodiments, applying and adhering the stent may be performed simultaneously. For example, a physician may apply the stent with the adhesive layer such that the inner layer of the stent conforms to the external surface of the organ while the adhesive layer simultaneously adheres the inner layer to the external surface of the organ.

In other embodiments, method 500 may be performed without step 506—that is, without adhering the passive stent. For example, upon application of the vacuum in step 508, surface tension between an external surface of the organ and the inner layer of the stent may adhere the stent to the external surface (e.g., as shown in FIG. 4F) without any additional or separate adhering. Accordingly, in such embodiments, step 508 of method 500 (described below) may be performed after step 504.

At step 508, a vacuum is applied to the passive stent configured to cause a plurality of components of at least one layer, e.g., the middle layer, of the passive stent to interlock and/or compress to rigidify. For example, a port through middle layer and/or the inner layer and/or the outer layer with tubing extending from the port to the middle layer, may allow for application of the vacuum. The port may be self-sealing after application of the vacuum or may include a removable seal.

Method 500 may comprise additional steps. For example, method 500 may comprise monitoring an air pressure between the external surface of the organ and the inner layer. For example, a barometer, piezoelectric sensor, or any other device for measuring air pressure may monitor the volume between the external surface of the organ and the inner layer. In such embodiments, an indication of an increase in air pressure based on the monitoring may trigger remedial action. For example, in embodiments where a vacuum is used, at least in part, to adhere the inner layer to the external surface, a pump may automatically apply additional suction to the volume between the external surface of the organ and the inner layer to remedy a reduction in or loss of surface tension. Alternatively, a physician or user may receive an alert in response to the indication of increase in air pressure and apply additional suction using a vacuum to remedy a reduction in or loss of surface tension. In embodiments where only surface tension between the external surface of the organ and the inner layer is used for adhering the same, a pump may still be used as described above to remedy a reduction in or loss of that surface tension.

In accordance with another method, a method for retaining an organ of a patient in an expanded state is provided comprising a) providing a brace having an inner layer, an outer layer and a middle layer positioned between the inner layer and outer layer, the middle layer comprising at least one or more soft components; b) applying a cover to the brace, the cover extending beyond a periphery of the device; c) applying a vacuum to provide a fluid tight seal of the cover to the skin; and d) subsequently applying a vacuum to the middle layer to rigidify the one or more soft components.

The foregoing description has been presented for purposes of illustration. It is intended that the specification and examples be considered as exemplary only. It is not exhaustive and is not limited to precise forms or embodiments disclosed. Other embodiments will be apparent to those skilled in the art from consideration of the specification and practice of the embodiments disclosed herein. Modifications and adaptations of the embodiments will be apparent from consideration of the specification and practice of the disclosed embodiments.

The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

The features and advantages of the disclosure are apparent from the detailed specification, and thus, it is intended that the appended claims cover all systems and methods falling within the true spirit and scope of the disclosure. As used herein, the articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Persons skilled in the art will understand that the elements and features shown or described in connection with one embodiment may be combined with those of another embodiment without departing from the scope of the present disclosure and will appreciate further features and advantages of the presently disclosed subject matter based on the description provided.

Throughout the present disclosure, terms such as "approximately," "generally," "substantially," and the like should be understood to allow for variations in any numerical range or concept with which they are associated. For example, it is intended that the use of terms such as "approximately" and "generally" should be understood to encompass variations on the order of 25% (e.g., to allow for manufacturing tolerances and/or deviations in design).

Although the apparatus and methods of the subject disclosure have been described with respect to preferred embodiments, those skilled in the art will readily appreciate that changes and modifications may be made thereto without departing from the spirit and scope of the present disclosure.

What is claimed is:

1. A brace for retaining an organ of an individual in an expanded state comprising:
   an inner layer configured to adhere to the organ using one or more of surface tension, vacuum or adhesive;
   an outer layer; and
   at least one sheet of paper forming a middle layer between the inner layer and outer layer, the at least one sheet of paper being enclosed and configured to rigidify upon application of a vacuum, wherein the at least one sheet of paper of the middle layer is crimpled, wrinkled, and/or pre-folded for rigidification;
   wherein the brace is dome shaped and configured to accommodate the organ in the expanded state.

2. The brace of claim 1, wherein each sheet of the least one sheet of paper has a thickness of about 0.001 inches.

3. The brace of claim 1, wherein the at least one sheet of paper is moldable to a contour of a patient's body.

4. The brace of claim 1 where the at least one sheet of paper is composed of multiple interweaved elongated strips restrained at the periphery and freely movable past each other prior to vacuum application.

5. The brace of claim 1, wherein the at least one sheet of paper is smooth and devoid of irregularities on its surface.

6. The brace of claim 1, wherein the at least one sheet of paper is soft and malleable prior to application of vacuum.

7. The brace of claim 1, wherein the at least one sheet of paper comprises a plurality of sheets of paper having a combined thickness of between about 5 mm to about 6 mm prior to rigidifying by vacuum.

8. The brace of claim 1, wherein the at least one sheet of paper is translucent.

9. The brace of claim 1, further comprising a port configured for applying the vacuum to the middle layer through at least one of the inner layer and the outer layer and tubing communicating with the port, the tubing having a plurality of perforations and extending into the middle layer.

10. The brace of claim 1, further comprising an interposed padding layer connecting the inner layer to the skin of the individual, the padding configured to evenly contact the organ and provide a buffer between the inner layer and organ to limit imprint of wrinkles on a skin of the patient.

11. The brace of claim 1, wherein the outer layer has a rim about at least a portion of its periphery and the brace further comprises an adhesive sheet placed over a least a portion of the rim and extending laterally outwardly from the rim for attaching and providing an air tight seal.

12. The brace of claim 1, wherein the outer layer has a rim about at least a portion of its periphery and the rim is a gel filled bladder with an adhesive outer layer for providing an air tight seal.

13. A device for retaining an organ of an individual in an expanded state comprising:
   an inner layer configured to adhere to the organ via one or more of a) a vacuum applied between an inner layer and the organ; b) surface tension between the inner layer and organ; or c) an adhesive contacting a skin of the individual;
   an outer layer having a rim about at least a portion of a periphery; and at least one or more components forming a middle layer between the inner layer and outer layer, the at least one or more components being enclosed and configured to rigidify upon application of a vacuum; and a cover attached to a least a portion of the rim of the outer layer, the cover having an adhesive and extending radially outwardly from the rim to adhesively attach to the skin of the individual such that it can maintain a vacuum seal that holds the organ in the expanded state without an adhesive between the skin and the inner layer;

wherein the device is dome shaped and configured to accommodate the organ in the expanded state.

14. The device of claim 13, wherein the adhesive is outside an area of where vacuum is applied between the inner layer and skin.

15. The device of claim 13, wherein an inner surface of the cover is covered by a peel away layer of material.

16. The device of claim 15, wherein the cover is removable and replaceable by another cover.

17. The device of claim 16, wherein the tubing has a non-linear configuration.

18. The device of claim 16, wherein the device is flexible and wherein the middle layer is configured to substantially conform to an external surface of the organ prior to rigidifying, and the middle layer is configured to maintain the organ in the expanded state after rigidifying.

19. A device for retaining an organ of an individual in an expanded state comprising:

an inner layer configured to adhere to the organ via one or more of a) a vacuum applied between an inner layer and the organ; b) surface tension between the inner layer and organ; or c) an adhesive contacting a skin of the individual;

an outer layer; and at least one or more components forming a middle layer between the inner layer and outer layer, with at least one or more components being enclosed and configured to rigidify upon application of a vacuum, the application of vacuum forcefully reduces the radial thickness of the one or more components of the middle layer; and a tubing positioned within the middle layer, the tubing having a plurality of openings for applying vacuum to the middle layer to rigidify the one or more components;

wherein the device is dome shaped and configured to accommodate the organ in the expanded state.

\* \* \* \* \*